United States Patent
Segman

(10) Patent No.: US 9,402,546 B2
(45) Date of Patent: *Aug. 2, 2016

(54) OPTICAL SENSOR DEVICE AND IMAGE PROCESSING UNIT FOR MEASURING CHEMICAL CONCENTRATIONS, CHEMICAL SATURATIONS AND BIOPHYSICAL PARAMETERS

(71) Applicant: CNOGA HOLDING LTD., Or Akiva (IL)

(72) Inventor: Yosef Segman, Zichron Yaacov (IL)

(73) Assignee: CNOGA HOLDINGS LTD., Or Akiva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/444,685

(22) Filed: Jul. 28, 2014

(65) Prior Publication Data

US 2014/0336478 A1    Nov. 13, 2014

Related U.S. Application Data

(63) Continuation of application No. 13/674,033, filed on Nov. 11, 2012, now Pat. No. 8,792,948, which is a continuation of application No. 11/909,158, filed as application No. PCT/IL2006/000379 on Mar. 26, 2006, now Pat. No. 8,335,550.

(60) Provisional application No. 60/664,957, filed on Mar. 25, 2005.

(51) Int. Cl.
*A61B 5/1455*    (2006.01)
*A61B 5/00*    (2006.01)
(Continued)

(52) U.S. Cl.
CPC .............. *A61B 5/0077* (2013.01); *A61B 5/0059* (2013.01); *A61B 5/02* (2013.01);
(Continued)

(58) Field of Classification Search
CPC ...... A61B 5/1455; A61B 5/0059; A61B 5/72; G01N 33/00; G06F 19/00
See application file for complete search history.

(56) References Cited

U.S. PATENT DOCUMENTS 6,491,628 B1 *  12/2002  Kobayashi ......... A61B 1/00059
                                                                600/168

*Primary Examiner* — Eric Winakur
(74) *Attorney, Agent, or Firm* — Mark M. Friedman

(57) ABSTRACT

Optical sensor devices, image processing devices, methods and computer readable code computer-readable storage media for detecting biophysical parameters, chemical concentrations, chemical saturations, vital signs and physiological information such as a malignant condition are provided. In some embodiments, the optical sensor includes an array of photodetectors, where each photodetector is configured to detect a spectrum of light. In some embodiments, the image processing device receives a live still or video electronic image, or alternatively, the electronic image is provided from an electronic storage media. Exemplary physiological parameters include but are not limited to a pulse rate, a biophysical or physiological property of skin, a cardiovascular property, a property related to an organ such as the liver or the kidneys, and a temperature fluctuation. In some embodiments, the physiological parameter is indicative of a malady including but not limited to an autoimmune disease, a cancer, a nutritional deficiency, a malignant condition of bone marrow, a present of an infectious microbe such as a fungus, a present of hepatitis, and a cardiovascular disorder a pulmonary disorder. Exemplary chemical concentrations include but are not limited to a chemical saturation, a pH level, a pH level in blood vessels such as capillaries or in skin, a glucose level such as a blood glucose level, a urea nitrogen level such as a blood urea nitrogen level, a $CO_2$ level such as a blood $CO_2$ level or a $CO_2$ saturation level, and an oxygen level such as a blood oxygen level or a blood oxygen saturation level. In some embodiments, the biophysical parameter, physiological parameter or chemical concentration is obtained from reflecting light from tissue from a mammalian subject. Alternatively one or more of these parameters are detected from a food item such as food tissue, a consumable beverage such as an alcoholic beverage, a dairy product, wine, a baked good, a fruit and a vegetable. Exemplary parameters related to food items include but are not limited to a parameter indicative of cooking or spoilage, a pH, a concentration of an antioxidant, and a concentration of an anti-inflammatory agent.

20 Claims, 10 Drawing Sheets

(51) Int. Cl.

| | | |
|---|---|---|
| *A61B 5/145* | (2006.01) | |
| *G06T 7/00* | (2006.01) | |
| *A61B 5/02* | (2006.01) | |
| *A61B 5/0205* | (2006.01) | |
| *A61B 5/021* | (2006.01) | |
| *A61B 5/08* | (2006.01) | |
| *H01L 27/146* | (2006.01) | |

(52) U.S. Cl.
CPC .......... *A61B 5/0205* (2013.01); *A61B 5/02141* (2013.01); *A61B 5/08* (2013.01); *A61B 5/1455* (2013.01); *A61B 5/14532* (2013.01); *A61B 5/14546* (2013.01); *A61B 5/14552* (2013.01); *A61B 5/411* (2013.01); *A61B 5/417* (2013.01); *A61B 5/4244* (2013.01); *A61B 5/443* (2013.01); *A61B 5/444* (2013.01); *A61B 5/445* (2013.01); *G06T 7/0012* (2013.01); *H01L 27/146* (2013.01); *G06T 2207/30004* (2013.01)

OPTICAL SENSOR DEVICE AND IMAGE PROCESSING UNIT FOR MEASURING CHEMICAL CONCENTRATIONS, CHEMICAL SATURATIONS AND BIOPHYSICAL PARAMETERS

This US nonprovisional patent application is a Continuation of U.S. patent application Ser. No. 13/674,033 filed Nov. 11, 2012 by the same inventor/applicant, which is continuation of U.S. patent application Ser. No. 11/909,158 filed Sep. 27, 2007 and issued as U.S. Pat. No. 8,335,550, which is a national phase of PCT/IL2006/000379 filed Mar. 26, 2006, which claims priority of U.S. Provisional Application No. 60/664,957 filed Mar. 25, 2005.

FIELD OF THE INVENTION

The present invention relates to image processing units and optical sensor devices for obtaining biophysical, biochemical, physiological and vital sign information from an array of photodetectors or from video image data including stored video image data.

BACKGROUND OF THE INVENTION

Diagnostic Medical Device

Diagnosis of physiological conditions by observing color, texture, and appearance of the skin, especially of the face, is a technique that has been used by physicians for generations and retains an important role today. Thus, the Medline Plus Medical Encyclopedia provided by National Institutes of Health advises physicians to "look for the presence of a pale complexion" when diagnosing sickle cell anemia. The NHS Direct Online Health Encyclopedia notes that "gray complexion" is a symptom of an impending heart attack. An online publication from the Dr. Joseph F. Smith Medical library discloses that "in many cases the diagnosis of jaundice is suggested by the appearance of the patient's eyes and complexion." The General Health Encyclopedia provided by Adam Inc. notes that a "very ruddy red complexion (plethoric)" is a symptom of hyperviscosity.

The aforementioned techniques require an actual human physician to view the patient or an image of the patient and to make the diagnosis. The human physician views the patient in sunlight or in a lit room, senses the color, texture, and appearance of the skin using photoreceptors within his or her retina, and analyzes the biofeedback of the skin to a natural continuous light (sun light) or artificial continuous or discontinuous spectrum of light in order to make a diagnosis. Unfortunately, human physicians are limited to light in the visible spectrum, are expensive, and prone to errors.

Historically, medical diagnosis was the domain of human physicians unaided by electronic devices. In the past century, with the advent of electric and electronic diagnostic devices, these devices have played a more prominent role. One example of such a diagnostic device is the oximeter for measuring the oxygen status of blood. In contrast to the human retina which is configured to detect continuous or discontinuous spectra of light, oximeters provide a coherent light source for emitting light at a pre-specified wavelength, and a detector for detecting light at this wavelength.

Pulse oximetry is a widely accepted noninvasive procedure for measuring the oxygen saturation level of arterial blood, an indicator of oxygen supply. A pulse oximetry system generally consists of a probe attached to a patient, a monitor, and a cable connecting the probe and monitor. Conventionally, a pulse oximetry probe has both a coherent lightsource such as an LED for emitting red and/or infrared light of predetermined wavelengths and a photodiode detector. The probe is typically attached to a patient's finger or toe, or a very young patient's foot. For a finger, the probe is configured so that the emitters project light through the fingernail, the arteries, vessels, capillaries, tissue and bone. The photodiode is positioned opposite the LED so as to detect the LED transmitted light as it emerges from the finger tissues.

The pulse oximetry monitor (pulse oximeter) determines oxygen saturation by analyzing the differential absorption by arterial blood of the two wavelengths emitted by the probe. The pulse oximeter alternately activates the probe LED emitters and reads the resulting current generated by the photodiode detector. This current is proportional to the intensity of the detected light. The pulse oximeter calculates a ratio of detected red and infrared intensities, and an arterial oxygen saturation value is empirically determined based on the ratio obtained. The pulse oximeter contains circuitry for controlling the probe, processing the probe signals and displaying the patient's oxygen saturation and pulse rate.

Pulse oximeters are described in U.S. Pat. No. 5,632,272, incorporated herein by reference in its entirety. US 2003/0009090 discloses an oximetry device which purportedly incorporates effects due to light scattering by red blood cells.

Oximeters are based upon the Beer Lambert law, which is given by:

$$\frac{c_{HbO_2}}{c_{HbO_2}+c_{Hb}} = \frac{A_1 I - A_2}{B_1 I - B_2}. \tag{1a}$$

The parameters $A_1$, $A_2$, $B_1$ and $B_2$ depend on the light absorption at two distinct wavelengths $\lambda_1$ and $\lambda_2$, while the ratio between absorption at two different ratios is given by I $$I = \frac{\log(I_1 e^{-<\vec{A},\vec{C}>})}{\log(I_2 e^{-<\vec{B},\vec{C}>})}. \tag{1b}$$

The symbol $c_{HbO_2}$ represents the oxyhemoglobin concentration ($HbO_2$) and $c_{Hb}$ represents the reduced hemoglobin concentration Hb.

The pulse of the subject can be determined by observing temporal patterns in an instantaneously measured arterial blood oxygen saturation level.

There is an ongoing medical need for non-invasive devices for detecting physiological information of a subject. Preferably, these devices would incorporate low cost, readily available components. Preferably, these non-invasive devices would also be operative at a distance from the subject, obviating the need to physically attach specific probe to the subject. Preferably, these non-invasive devices would be operative to detect a wide range of physiological indications.

Devices for Estimating Relevant Biophysical and Biochemical Parameters in Food and Beverage There is an ongoing need for techniques for analyzing relevant biophysical and biochemical parameters of food and beverages, especially perishable items such as fruit and vegetable produce, perishable dairy products, meat and fish products as well as less perishable items such as wines such as wines provided within sealed bottles. Although it is known that wine color in some situations can be a good predictor of wine quality, assessment of wine quality from visual characteristics of wine requires trained experts who are limited to subjectively reporting qualitative characteristics rather than a quantitative indication of wine quality like a pH. Furthermore, it is known that a spoilage status of food such as meat is also related to meat color. For the specific case of beef, psychrotrophic bacteria at the meat surface leads to oxidation of meat pigments which results in a progressive deterioration of the acceptable red color and the appearance of varying degrees of brown surface discoloration.

There is an ongoing need for methods and apparatus for detecting biophysical properties of food products and beverages.

Devices and Methods for Estimating Relevant Biophysical and/or Biochemical Parameters in Environmental Contamination Chemical contamination and environmental pollution threatens our existence everyday, everywhere. There is an ongoing need for environmental hazard detectors, and in particular, cost effective, easy to operate of environmental hazard detectors. For example, there is an ongoing need for devices and methods for detecting a level of contaminative substances in liquids and/or in gases. For example, there is an ongoing need for devices and methods for detecting a level of an pollution.

SUMMARY OF THE INVENTION

Some or all of the aforementioned needs, and other needs, may be satisfied by several aspects of the present invention.

The present inventor is now disclosing methods and devices for measuring biological, biophysical, physiological and/or chemical parameters in accordance with electric signals generated from an array of photodetectors.

According to some embodiments, the photodetectors are configured to detect a spectrum of light.

According to some embodiments, the photodetectors are configured to receive light which is scattered from and/or reflected from (partially reflected or and/or traverses an object or substance—for example, tissue of a subject (for example, a mammalian subject) and/or biological matter (for example, biological tissue or tissueless biological matter) and/or a liquid and/or food and/or beverages According to some embodiments, the generated electrical signal is processed (for example, by a signal processing or image processing unit), and electrical output indicative of a value of the parameter is generated, for example, using one or more routines disclosed herein.

The photodetectors may measure light reflected from and/or partially traversing a measured object. The light source may be artificial light or sun light and the image sensor is a regular image sensor (e.g. CMOS or CCD) having wide frequency range covering the UV and IR areas as well.

According to some embodiments a biophysical marker is a biochemical concentration.

Exemplary measured parameters include but are not limited to O2 saturation, and Co2 Saturation, pH, a level of a saccharide such as glucose, a concentration of a substance, a red cells count (number of estimated red cells per cubic millimeter), a skin risk diagnostic parameter, moisture, dryness, clarity, color vividness and saturation.

Skin Risk Diagnostic Parameters

According to some embodiments, a "skin risk diagnostic parameter" is indicative of a probability or likelihood of that a region or regions of skin or other soft tissue will generate a specific physiological condition (for example, will exhibit new pigmentation spot or spots and/or will exhibit malady (for example, a cancerous condition) or will exhibit a susceptibility to a disease (for example, a precancerous condition) when subjected to a direct and/or non direct light such as sun light, for example, a given quantity and/or type of light for a given period of time. For example, on a hot day white or Caucasian skin tissue has an average higher risk than a black skin tissue to generate pigmentation spots (or any other skin disease e.g. melanoma).

The present inventor is disclosing for the first time a method, device and computer readable code for measuring skin risk diagnostic parameters from video images and/or electrical signals generated by an array of photodetectors.

Optionally, electronic output indicative of a suggested skin treatment regimen for treating and/or preventing and/or lowering the risk of skin generating new pigmentation spots and/or becoming diseases and/or becoming associated with a pre-disease state may be generated. In some embodiments the analysis provides analysis on the current skin pigmentation biophysical status for suggesting treatment for reducing the number of pigmentation spots.

Thus, in some embodiment the pigmentation diagnostic provides future risk probability for suggestion sun protection. Based on the system skin physiological analysis and by estimating the sun light frequencies including heat conditions a presently disclosed system may be operative to suggest one or more current risk factors in exposing the skin over certain time and to recommend certain sun protection (or protection from any other light source).

General Discussion

Exemplary physiological conditions and/or parameters measured include but are not limited to cardiovascular conditions such as pulse, blood pressure and a pulse transition time (PTT), red cells count (number of estimated red cells per cubic millimeter), conditions related to blood physiology such as O2 blood saturation level, blood glucose level, blood CO2 level, a blood pH and a blood urea nitrogen level, conditions related to kidney function such as blood urea nitrogen level, conditions related to liver function such as bilirubyn level, condition related to skin disease such as psoriasis or melanoma are reflected by several skin physiological parameters such Oxygen and carbon dioxide concentration, local skin blood systolic and diastolic blood pressure, stroke volume variation (i.e. volume of blood pumped per stroke) parameters (for example, a parameter indicative of the absolute volume per individual stroke or pluralities of strokes, or a parameter indicative of a function of the individual volumes pumped by multiple strokes, for example, a stroke volume average, stroke volume variation, or a higher order moment stroke volume) skin pH, skin moisture (Oil) and dryness (water), local skin capillary glucose, skin color vividness, skin saturation and skin local deformation and conditions related to skin physiology for cosmetic treatment such as oil moisture content of skin, skin dryness, skin absorption potential, skin pigmentation, red cells concentration, blood pressure, skin pH, skin saltiness level, skin saturation, skin vitality and skin vividness.

Not wishing to be bound by any theory, it is noted that in the presence of certain maladies such as cancer, cardiovascular disease and autoimmune disease, certain chemical concentration are altered from normal levels by, for example, cancer cells, and thus the presently disclosed devices, software and methods for measuring chemical concentrations and saturations as well as specific biophysical parameters are useful in detection of biophysical parameters indicative of these maladies., and thus are useful in the detection of these maladies.

Thus, it is noted that an abnormal hemoglobin level can be caused by a number of factors. Some common reasons include a nutritional deficiency, a malady of the colon such as bleeding colon cancer, certain tumors, a disored to the bone marrow such as polycythemia rubra vera, and abuse of a drug such as eryhtopoietin (epogen).

In some embodiments some or all photodetectors are configured to detect a spectrum of light. In some embodiments, each photodetector is characterized by an absorption distribution functions which decays outside of a finite range. Video images from any wavelength are appropriate for the appropriate invention. Appropriate spectra include but are not limited to the visible spectrum, the IR spectrum, and UV spectrum and the thermal spectrum.

Not wishing to be bound by theory, it is now disclosed that video input of human skin provides a tremendous amount of information about the human body physical and other tissue less condition. Skin cells are part of the human body and therefore contain information about the physical status of the body. Thus, the spatial temporal color space of the video image signal of a human body from various locations including the face is indicative of the physiological status of the human under consideration.

According to some embodiments, a parameter is determined from a food item including but not limited to a beverage, a consumable alcoholic beverage such as wine, a fermented beverage, beer, hard liquor and whiskey, produce such as fruit and vegetables, a meat item, fish, eggs, a baked item. According to some embodiments, light is received from a tissue-less substance such as a liquid.

In some embodiments, the measured parameter relates to wine or beverage such as a consumable alcoholic beverage such as wine include but are not limited wine pH, wine glucose, wine clarity, wine color vividness and chemical saturation.

In some embodiments, the measurement parameter is relates to a biological phenomena such as food quality, food spoilage, and cooking of food.

Exemplary food and beverages include but are not limited to food comprising animal and/or vegetable tissue and tissue-less beverages.

The present inventor is for the first time disclosing devices and methods for extracting this relevant physiological from an electronic still or video image of a subject. Thus, embodiments that provide optical sensors for sensing at least two different spectral ranges wavelengths allow detection of biophysical physiological data gleaned from the image.

In some embodiments, the array of optical sensor device includes an image sensor Exemplary image detectors includes but are not limited to CMOS image sensors and CCD image sensors at various wavelength sensitivity such the visual range (380 nm to 800 nm), lower or higher than the visual range such as from ultra violate (280 nm or below) to NIR (Near IR 1200 nm and above 1200 nm).

The disclosed optical sensor device of the present invention is configured to obtain biophysical physiological information about the subject by detecting light of any wavelength. In some embodiments, the photodetectors or image sensors of the currently disclosed device are configured to sense light of a wavelength between 280 nm to 1200 nm. In some embodiments, the photodetectors or image sensors of the currently disclosed device are configured to sense light of a wavelength less than 300 nm. In some embodiments, the photodetectors or image sensors of the currently disclosed device are configured to sense light of a wavelength greater than 1200 nm.

It is disclosed that the disclosed optical sensor device is also operative by sensing ambient light reflected from and/or traversing the soft tissue, skin or inner tissue such as endothelial tissue of the subject without any specific need to provide a light source. Nevertheless, in some embodiments, an optional light source for transmitting a spectrum of light to be reflected from the skin, soft tissue of the subject is provided.

Although in some embodiments the present invention provides an optical sensing device, the present invention is not limited to sensing devices. According to some embodiments, an image processing unit and/or a computer readable storage containing instruction data is provided. In some embodiments, the image processing unit and/or optionally instruction data is configured to detect a biophysical physiological condition of a previously obtained image of a subject, and there is no need whatsoever to provide the actual subject in order to generate output indicative of the physiological condition of the subject.

In some embodiments, the photodetectors and/or optical detectors are operative to receive scattered light from a measured object (for example, a mammalian subject and/or biological matter and/or a liquid, etc).

As used herein, "scattered light" refers to any combination of light is either reflected from an object and/or traverses through the object and/or partially traverses and/or partially reflected from or by the object.

It is disclosed that, in some embodiments, the disclosed optical sensor device may be operative to sense scattered ambient light from the soft tissue (for example, skin or inner tissue such as endothelial tissue or blood tissue) of the subject. Thus, in some embodiments, there is no need to provide a specific light source, and ambient light (for example, day light and or room light). Alternatively or additionally, a specific light source is provided, and scattered light from the light source and/or ambient light may be detected. Thus, in some embodiments, an optional light source may be provided. In some embodiments, this optional light source is configured to transmitting a spectrum of light to be scattered by (i.e. reflected and/or traversing and/or the combination thereof) the soft tissue.

It is noted that there is no limitation on the distance between the light source and the target tissue and/or liquid and/or object to be analyzed. Thus, in exemplary embodiments, the light source may be contacted (or almost contacted, i.e. less than 1 cm, or less than 1 mm from) this object. In other embodiments, there may be any distance between the light and the object.

In some embodiments, the image processing unit and/or instruction data are configured to obtain biophysical physiological condition based upon archived digital image data still or such as video, optionally provided in non-volatile memory such as on a hard disk, in a flash memory device, video tape and the like. It is noted that the image processing unit and/or the optional instruction data do not necessarily provide current physiological information about the subject, but rather provide historical information in accordance with the physiological condition of the subject at the time that the image of the subject was produced.

Thus, it is noted that the subject need not even be alive, and the image processing unit and/or optional instruction data are configured to provide historical physiological information about the subject at the time of imaging.

It is now disclosed for the first time an image processing device for obtaining biophysical physiological information. According to some embodiments, the disclosed image processing device includes an image receiving unit for receiving a video digital image of soft tissue, skin or tissue less of a subject and an image processing unit for generating from the video digital image output indicative of a biophysical physiological condition of the subject, wherein the biophysical physiological condition is selected from the group consisting of a cardiovascular condition, a condition related to blood physiology, a physiological condition related to skin, skin temperature, a physiological condition related to kidney and liver function Furthermore, it is noted that in some embodiments the video digital image includes a single static video digital image. Alternately, the video digital image includes a dynamic time dependent video clip of soft tissue, skin or tissue less of the subject.

It is now disclosed for the first time computer-readable storage medium containing optional instruction data for obtaining physiological information about a subject. According to some embodiments, the optional instruction data comprises the instructions of processing a video digital image of tissue, food item liquid of a subject, and generating output indicative of a biophysical physiological condition of the mammalian subject, liquid, beverage or food item.

In some embodiments, the disclosed optical sensor device and/or image processing device further includes a database including expected values indicative of the biophysical physiological condition. Optionally, the device further includes an alarm device, for indicating when a measured value indicative of at least one biophysical physiological condition deviates from an expected value.

The presently disclosed devices and methods are also applicable for identifying an examined individual based upon measured physiological properties or examine certain food or liquid quality.

Thus, in some embodiments, the optical sensor device is for identifying a subject, and is thus operatively linked to a physiological information database for storing previously obtained physiological information about a plurality of subjects, and a comparison module, for comparing generated output indicative of at least one physiological condition of the subject with previously obtained physiological information.

It is now disclosed for the first time a method of identifying a subject. The disclosed method includes generating a video image of the subject, deriving from the video image information indicative of a biophysical physiological condition of the subject, and comparing information with previously stored information relating to physiological condition of the subject.

It is noted that there are a myriad of applications for the disclosed devices and methods that have not escaped the attention of the present inventor. Thus, it is noted that devices, software and methods of the present invention provide minimally invasive diagnostic tools for important medical vital life signs. Furthermore, it is noted that devices, software and methods of the present invention provide for ascertaining skin status conditions in order to improve and customize cosmetic treatments. Finally, it is noted that the monitoring of vital life signs from a distance is important in medical and security applications.

In some embodiments, the distance between the photo array sensor (e.g. CCD camera) and an object under consideration is limited up to the optical zoom available for closing up the object. Therefore, for some application where the object is positioned at distance say 1 km' from the photo array sensor it is possible to measure biophysical physiological status conditions. Thus for the first time it is shown a long distance touch free system for detecting biophysical physiological condition on an object under consideration.

Although some embodiments provide a touch-free system (i.e. the optical or photo sensor or detector, for example array, does NOT touch measured object, and may be any distance from almost touch to infinite), this is not a limitation of the present invention.

In some embodiments, the measured object may be at "zero" distance from a light source and/or the sensor array— the object may cover (partially or totally) the sensor or the sensor lens or the sensor glass. In some embodiments, at "zero" distance, light which traverse the object is detected. In some embodiments, a portion of the light traverses the object and a portion of the light is reflected.

According to some embodiments, the "array of photodetectors" are provided as part of a video camera.

In some embodiments, in accordance with electrical output from the photodetectors and/or a video image, a parameter related to chemical, substance and topological structure of various contamination substances may be measured. In some embodiments, an air pollution parameter (for example, a concentration of an air pollutant) may be measured.

These and further embodiments will be apparent from the detailed description and examples that follow.

DETAILED DESCRIPTION

Figure 1:
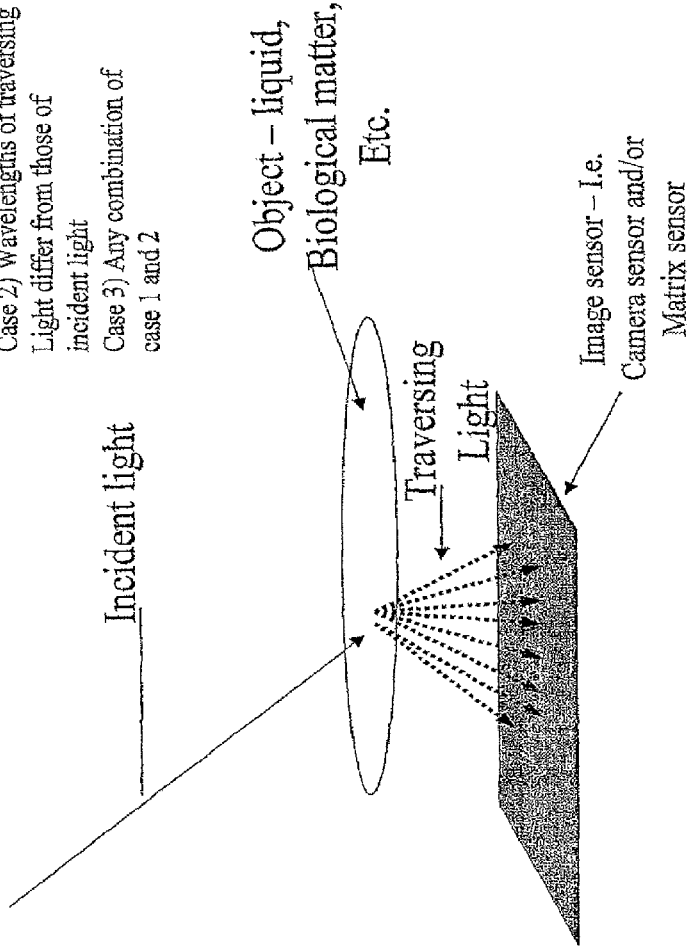
FIG. 1 describes ambient light transversing an object and being detected by an image sensor array. The distance of the object to the light source may depend on the source of light: for the case of sun light the distance is huge, and for an artificial light source the distance may be can be, for example, a few millimeters. The distance of the object from the image sensor array can be at any positive distance including zero distance.
Figure 2:
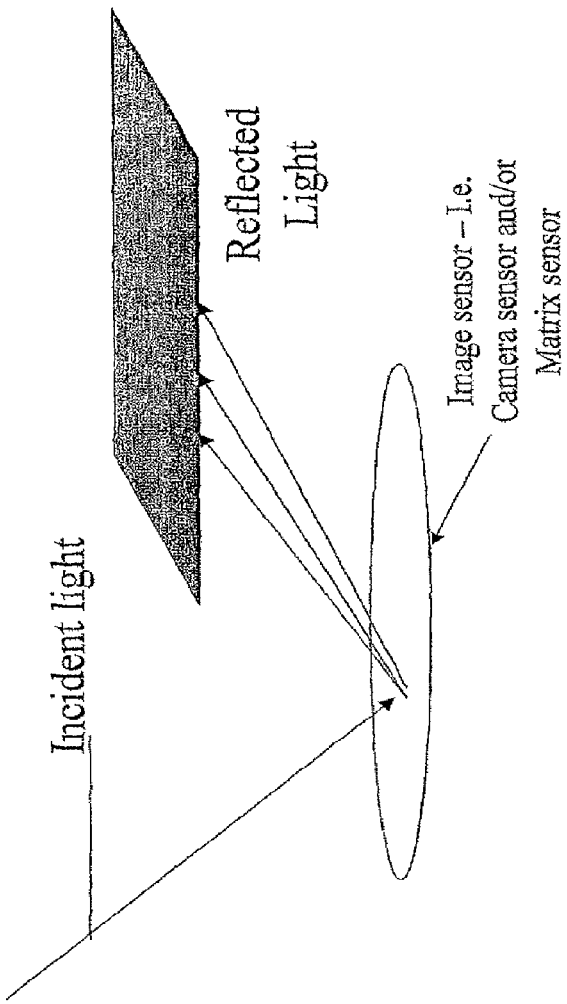
FIG. 2 describes ambient light from a source reflected by an object and detected by an image sensor array. The distance of the object to the light source may depend on the source of light: forthe case of sun light the distance is huge, and for an artificial light source the distance may be can be, for example, a few millimeters. The distance of the object from the image sensor array can be at any positive distance including zero distance.
Figure 3A:
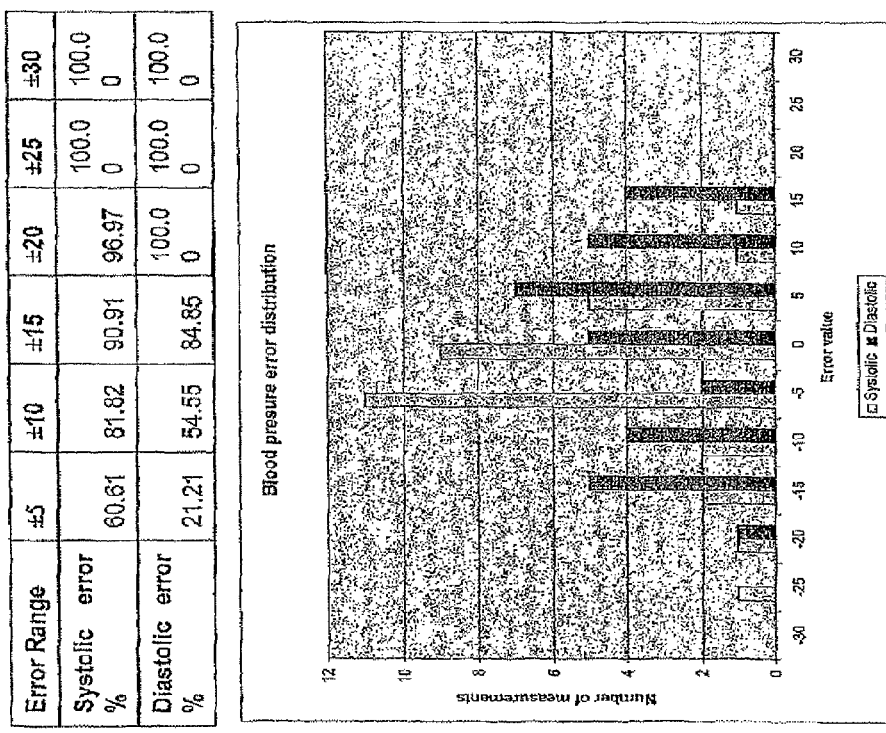
FIG. 3A presents blood pressure measurements and measured blood pressure error distribution obtained using video images and/or electrical output from photodetectors in accordance with some embodiments of the present invention (see example 14A).
Figure 3B:
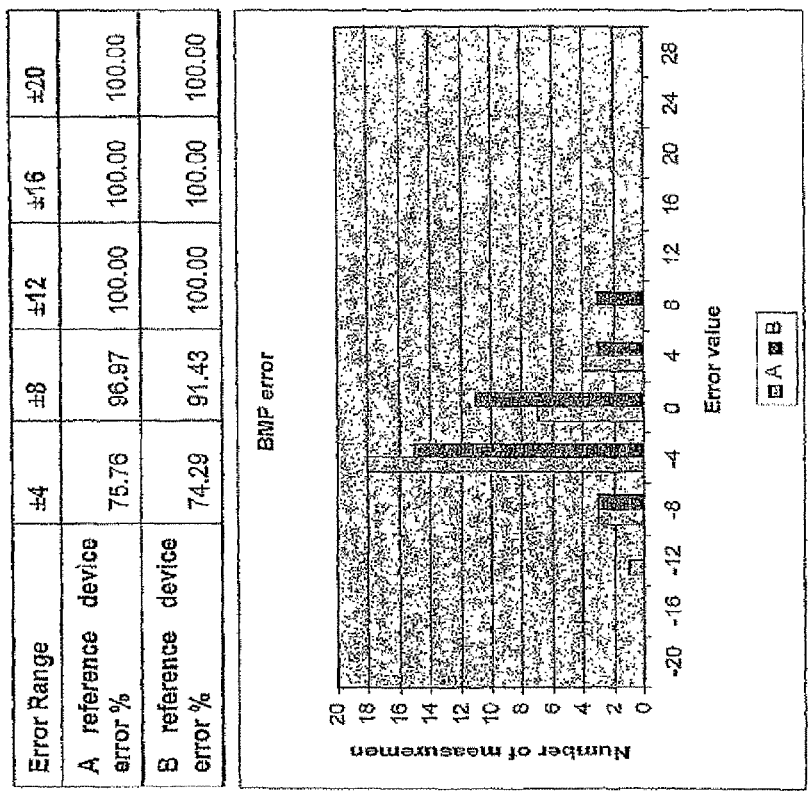
FIG. 3B presents heartbeat measurements and heartbeat measurement error obtained using video images and/or electrical output from photodetectors in accordance with some embodiments of the present invention (see example 14B).
Figure 3C:
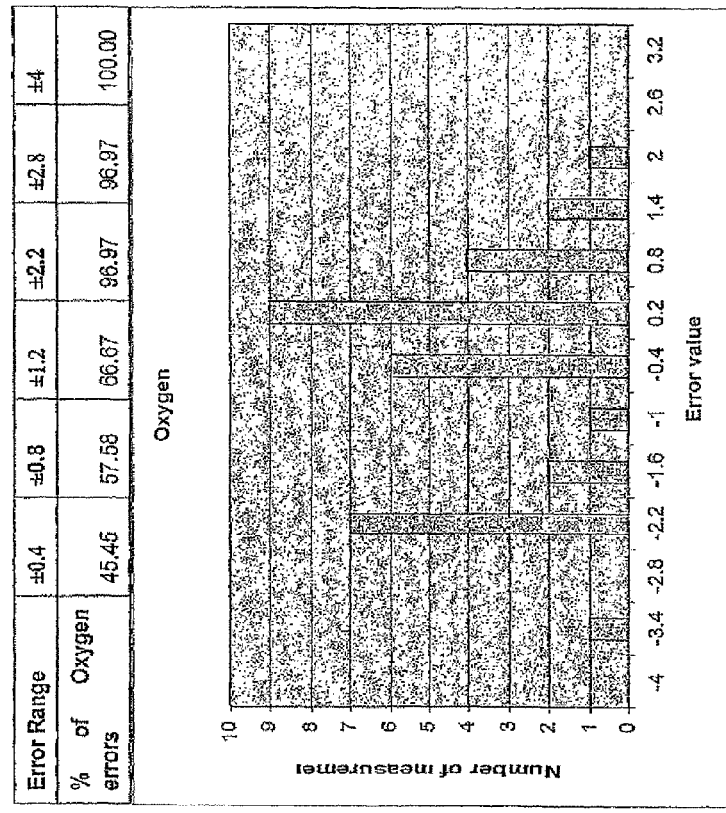
FIG. 3C presents blood oxygen level measurements and blood oxygen level measurement error obtained using video images and/or electrical output from photodetectors in accordance with some embodiments of the present invention (see example 14C).
Figure 3D:
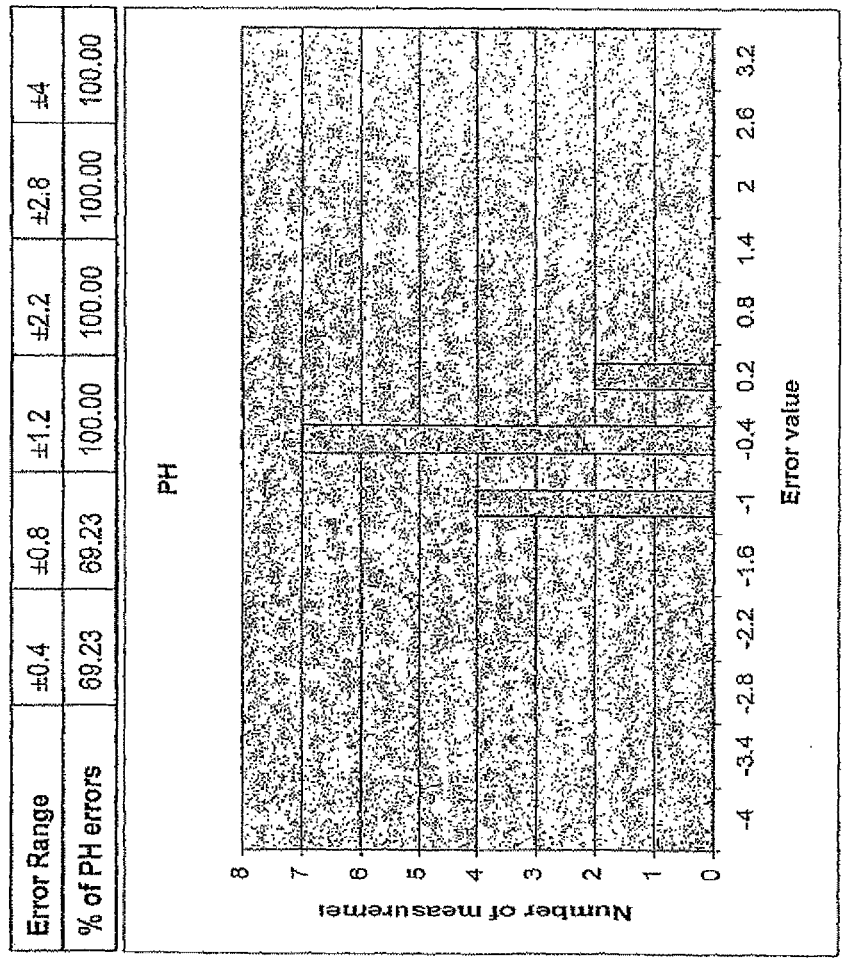
FIG. 3D presents skin pH measurements and skin pH measurement error obtained using video images and/or electrical output from photodetectors in accordance with some embodiments of the present invention (see example 14D).
Figure 4:
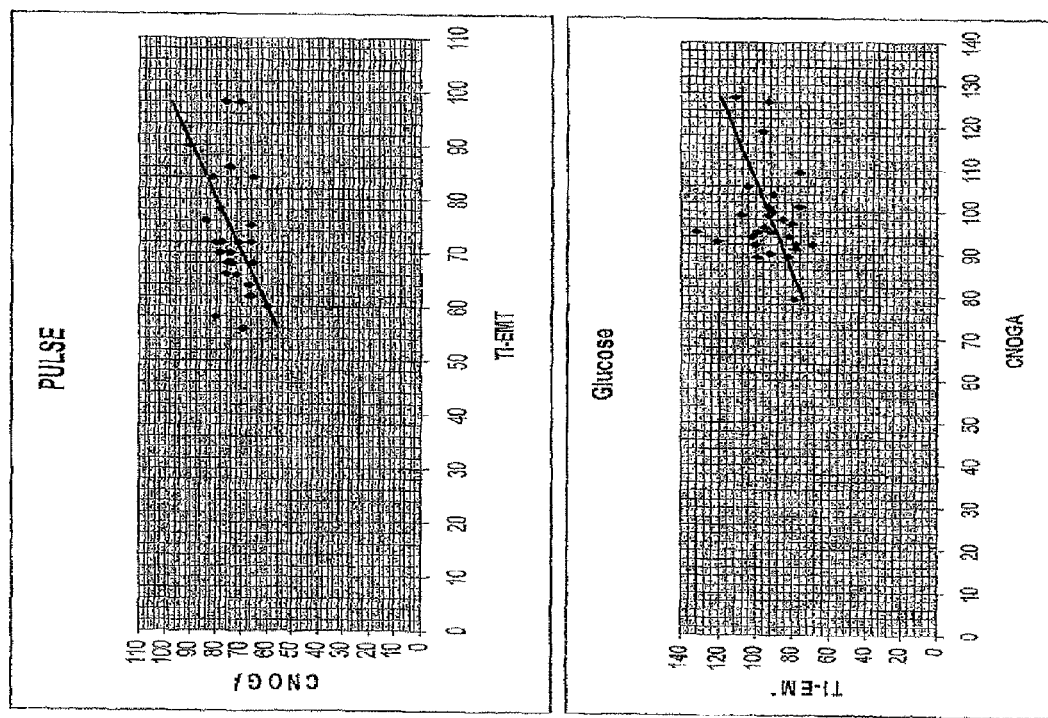
FIG. 4 provides graphs of measured pulse and glucose levels. (see example 16)
Figure 5A:
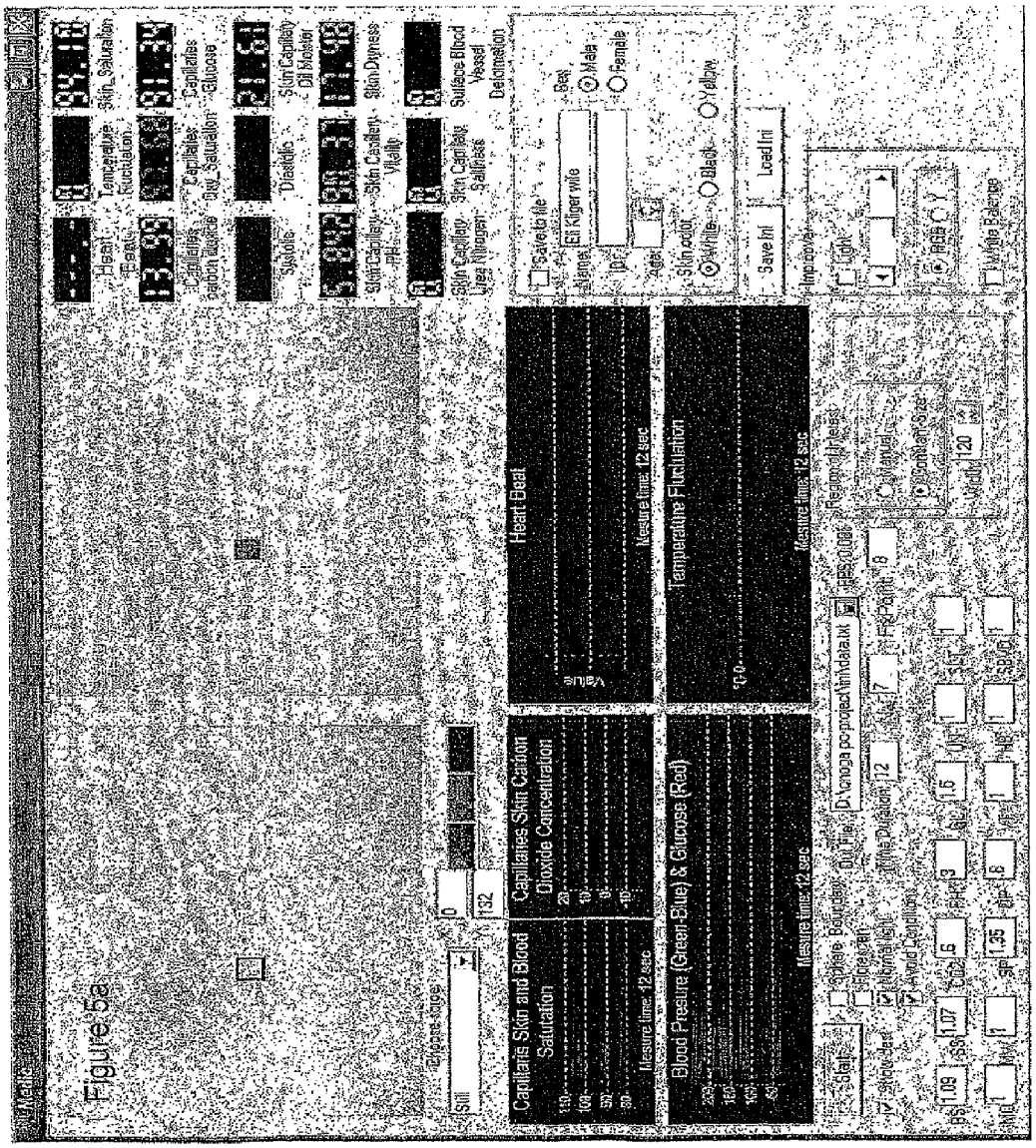
FIGS. 5A-5C present experimental measurement for melanoma. obtained using video images and/or electrical output from photodetectors in accordance with some embodiments of the present invention (see example 18).
Figure 5B:
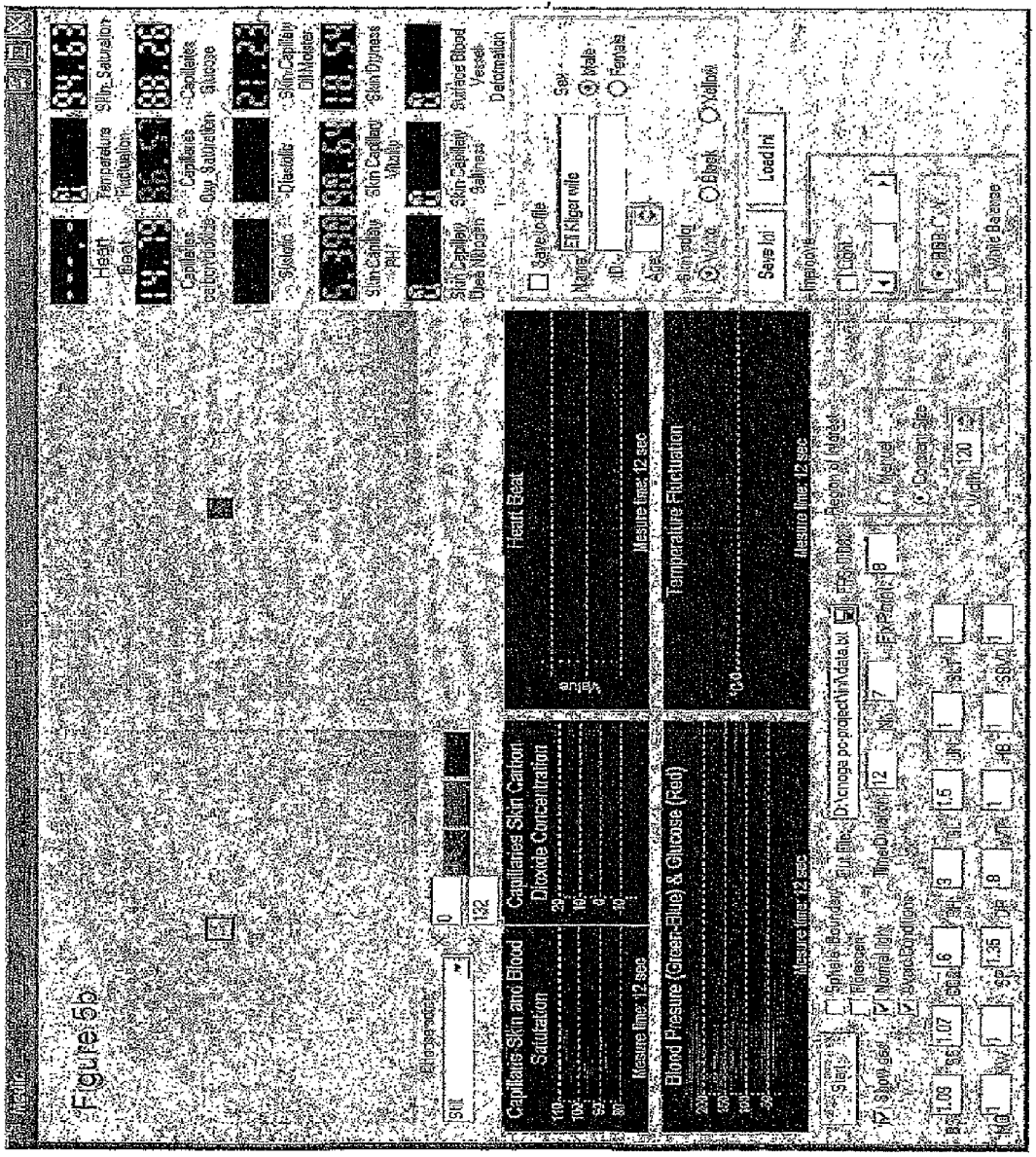
Figure 5C:
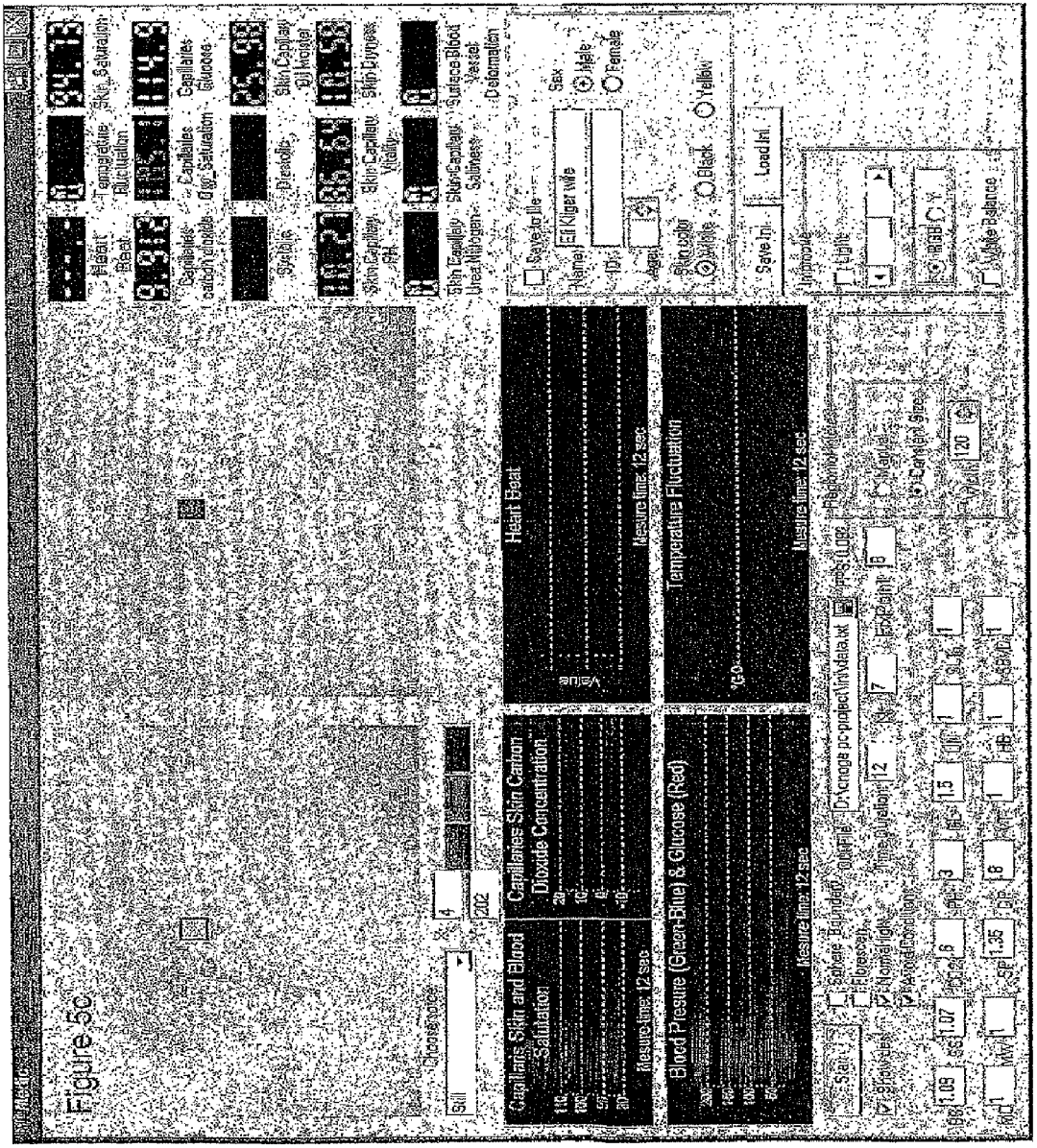

The present invention will now be described in terms of specific, example embodiments. It is to be understood that the invention is not limited to the example embodiments disclosed. It should also be understood that not every feature of the system, method and computer-readable code for detection and/or diagnosis is necessary to implement the invention as claimed in any particular one of the appended claims. Various elements and features of devices are described to fully enable the invention. It should also be understood that throughout this disclosure, where a process or method is shown or described, the steps of the method may be performed in any order or simultaneously, unless it is clear from the context that one step depends on another being performed first.

Skin cells and endothelial cells are part of the body and are nourished by blood and/or other bodily fluids. The biofeedback of blood-nourished skin and endothelial cells in response to a continuous and/or discontinuous spectrum of light is influenced by physiological and/or biophysical properties of the cells, such as a concentration of a substance in the cells or in the fluid nourishing the cells. The color properties (e.g. red, green and blue properties) of an individual cell or groups of cells are influenced by the biophysical properties of the cell as well as the biophysical Thus, it is possible to measure these physiological, biophysical and biochemical parameters by judiciously analyzing color properties of the cells.

Furthermore, by measuring temporal variations in derived variables related to biophysical properties of the cells, it is possible to obtain even more biophysical properties, such as biophysical properties of the circulatory system which supplies blood or other bodily fluid to the cells. Exemplary biophysical properties of the circulatory system include but are not limited to pulse, blood pressure, red cells count, stroke volume variation, and pulse transmission times. Thus, blood pressure is reflected locally over any local area in the body including any local skin surface indirectly generating systolic and diastolic color potential.

Relevant physiological or biophysical properties that can now be measured include but are not limited to local levels of O2, CO2, Urea Nitrogen, CO2, red cells count, pH, and glucose in tissue or bodily fluid such as blood. These physiological or biophysical properties are all indirectly connected to the spatial-temporal Red, Green, Blue colors, and their potential, intensity, irregularity, regularity, vividness, saturation, deformations, correlation, auto correlation, cross correlation, histograms, look up tables, diffusion, potential, heat, absorption, and derivations. Therefore, any sufficiently still image or video footage of a subject provides sufficient information about the human body condition. The present inventor is now disclosing for the first time that it is possible to estimate physiological and biophysical measurements from a electronic image data, both still image data obtained at a single instance in time, as well as image data comprising a series of images obtained at different instances in time.

Consider the more general case where the light source is the Sun natural light producing a continuous spectrum or artificial light such as white fluorescent tube which generate a discrete series of spectra or certain bandwidth limitation. In contrast, with a monochromatic light source, the bandwidth is focused into narrow interval. The white light takes wide spectrum. The presently disclosed devices and methods are appropriate when using both light sources.

The present inventor has found that by mathematically analyzing the biofeedback of certain soft tissue to natural light or artificial light, it is possible to measure concentrations of physiological relevant compounds within the subject, and to measure biophysical parameters related to the a physiological of the subject. The applications of the presently disclosed techniques are numerous, including applications in the fields of health care, cosmetics, security, forensics, and military applications.

Furthermore, the present inventor has found that by monitoring and analyzing the temporal development of biofeedback of certain soft tissue of mammalian subject that is exposed to natural or artificial light, it is possible to measure certain physiological parameters derived from the temporal development of a biophysical parameter. It is noted that any temporal biophysical parameter that can be measured with an oximeter can also be measured using the presently disclosed methods and devices.

The present inventor is also disclosing a plethora of applications of the presently disclosed apparatus and methods. Forensic applications includes methods and devices for determining a time of death. Military applications include a method and device for determining if a mammalian subject is a live or dead.

It is further noted that the present invention is not limited to detection of biophysical parameters of mammalian subjects. In some embodiments, devices and methods for measuring biophysical parameters of plants, fruits and vegetables are presently disclosed. In some embodiments, the present invention provides devices and methods for measuring biophysical parameters of foodstuffs including both foods and beverages. Exemplary beverages include but are not limited to alcoholic beverages such as wine and beer and hard liquor, and milk Exemplary foodstuffs include but are not limited to produce such as fruits or vegetables, meat such as beef, chicken, pork, lamb or fish, and dairy products such milk, yogurts, and cheeses.

Some Brief Definitions

According to some embodiments, a spectrum of light refers to a certain distribution function of light, either as a continuous spectrum or as a series of discrete spectra.

It is noted that any electrical or electronic signal disclosed herein as being generated or processed refers to both digital electronic signals as well as to analog signal.

According to some embodiments, a "desired" parameter is a parameter that is being measured or detected, such as a biophysical parameter, a chemical concentration or saturation, and a physiological parameter.

According to some embodiments, "skin" tissue refers to any tissue associated with the skin, include but not limited to dermal tissue and epidermal tissue.

According to some embodiments, a "pigment" refers to a substance, such as chlorophyll or melanin, that produces a characteristic color in plant or animal tissue.

According to some embodiments, a "temporal parameter" refers to a physiological or biophysical parameter which is estimated during time, such as the case of heartbeat pulse or a transition wave generated from the heartbeat pulse or from the breathing process or from the vessels circulation, etc.

As used herein, light traversing measured object (such as a liquid and/or a biological tissue) refers one or two or three cases—CASE 1—a portion of the light traverses the object and a portion of the light is reflected by the object onto and into the photodetector array; CASE 2—the light completely penetrates the object and then scattered onto and into the photodetector array (i.e. when the object completely covers the photodetector array. CASE—3 the light is completely reflected from the object onto and into the photodetector array. The light source in all cases can be natural and/or artificial light.

As used herein, determining a "concentration" or concentration profile includes determining the actual concentration (or concentration profile) and/or determining a known function of the concentration (or concentration profile).

As used herein, determining a "parameter" (for example, a physiological parameter or a biophysical parameter) includes determining the actual parameter and/or determining a known function of the parameter.

Discussion

Some embodiments of the present invention provide an optical sensor device for detecting a chemical or substance concentration, in or on a mammalian subject the device comprising:
   a) an array of photodetectors, each photodetector configured to detect a spectrum of light, said array for receiving light reflected from and/or traversing (i.e. at least partially traversing) a first tissue of the mammalian subject and for producing an electric signal; and
   b) a processing unit adapted to receive and electronically process said electric signal to generate output indicative of a concentration of a substance within or on the mammalian subject.

In some embodiments, the light completely traverses the measured object and/or the liquid and/or the biological tissue.

In some embodiments, the light partially traverses the measured object and/or the liquid and/or the biological tissue and partially reflected by the object.

In some embodiments, the light is completely reflected by the object.

According to some embodiments, each photodetector is configured to detect a continuous or discontinuous spectrum of light.

According to some embodiments, the mammalian subject is a human subject.

According to some embodiments, the processing includes generating an electronic image.

According to some embodiments, the chemical concentration is selected from the group consisting of a concentration of a molecule and a chemical saturation.

According to some embodiments, the chemical concentration is a local concentration.

According to some embodiments, the processing unit is operative to generate output indicative of said local concentration of said substance within a second tissue of the mammalian subject.

According to some embodiments, the tissue may be selected from the group consisting of a first tissue and a second tissue is selected from the group consisting of soft tissue, hard tissue, skin, surface tissue, outer tissue, internal tissue (for example, soft tissue, hard tissue such as bone, and liquid tissue (i.e. tissue suspended in a liquid such as blood tissue), a membrane, fetal tissue and endothelial tissue.

According to some embodiments, the processing unit is configured to generate output indicative a parameter selected from the group consisting of a glucose level, a pH level, a CO2 level, an oxygen level, an oxygen saturation level, red cells concentration, a CO2 saturation level, a bilirubin level, a skin saturation level, a concentration or saturation of salt, a concentration of an oily substance, and a urea nitrogen level.

According to some embodiments, the processing unit is adapted to generated output indicative of a collagen concentration, which may be related to the smoothness of the skin surface. Thus, in some embodiments, the smoothness of the skin surface (and, thus, a collagen concentration) may be quantified by performing a smoothness or sharpness analysis to an image acquired by the photodetector(s) and/or optical sensor(s). A follow up smoothness diagnostic may be effective in case of collagen treatment. One non-limiting example of a smoothness operation is a convolution operation in order to estimate the skin tissue smoothness (such as a gaussian filter).

Furthermore, it is noted that in some embodiments, the skin smoothness may be analyzed a plurality of times over a given period of time (for example, over a period of times that is at least a few days, or at least a week, or at least several weeks, or at least a month, or several months).

In particular embodiments, the subject whose collagen profile (i.e. collagen concentration and/or collagen concentration profile and/or a profile of a physical and/or chemical parameter of collagen such as cross-linking) is computed may be a subject undergoing a treatment (for example, a skin treatment, such as a skin tightening).

Thus, in exemplary embodiments, a method and device for determining the efficacy of a treatment regimen (for example, a skin treatment such as a skin tightening, for example, a surgical treatment and/or a treatment provided by electromagnetic radiation) and/or nutrition regimen (for example, related to collagen) is provided. A patient undergoing the treatment is selected, and a collagen parameter (for example, a collagen concentration and/or concentration profile) is monitored over time, for example, the collagen is monitored before and after various collagen treatments. By monitoring this collagen parameter over time, the effectiveness of the treatment may be monitored. Not wishing to be bound by theory, it is noted that this presently disclosed method and device may obviate the need for using ultra-sound techniques to monitor skin smoothness and/or collagen parameter(s).

According to some embodiments, the processing unit is operative to generate output indicative of a said concentration within bodily fluid of the mammalian subject.

According to some embodiments, the bodily fluid is selected from the group consisting of blood and sweat.

According to some embodiments, the processing unit is operative to generate output indicative of a said concentration within a circulatory system of the mammalian subject.

According to some embodiments, the processing unit is operative to generate output indicative of said a concentration within a blood vessel of said mammalian subject.

According to some embodiments, the processing unit is operative to generate output indicative of a said local concentration within a capillary of said mammalian subject.topological deformation of the blood vessels of said mammalian subject.

According to some embodiments, the said substance is dissolved or partially dissolved substance within a bodily fluid within the mammalian subject.

According to some embodiments, the dissolved or partially dissolved substance is an ion.

According to some embodiments, the processing unit is operative to generate output indicative of pH.

According to some embodiments, the substance is a pigment According to some embodiments, the substance is a waste product.

According to some embodiments, the substance is a polymer.

According to some embodiments, the substance is a complexed polymer.

According to some embodiments, the substance is a biopolymer.

According to some embodiments, the substance is a protein.

According to some embodiments, the substance is a complexed protein.

According to some embodiments, the complexed protein is selected from the group consisting of a hemoglobin-oxygen complex and a hemoglobin-carbon dioxide complex.

According to some embodiments, the substance is a saccharide.

According to some embodiments, the saccharide is glucose.

According to some embodiments, the local concentration of said substance is indicative of a physiological condition in the subject selected from the group consisting of a condition of the liver, a condition of the kidney cancer, a skin cancer, a blood cancer, a nutritional deficiency, a loss of blood, a malignant condition of bone marrow, dehydration, a cardiovascular condition, hepatitis, a physiological condition of a muscle, a presence of a microbe, a presence of an infectious microbe, an autoimmune condition, a presence of a fungus, and a pulmonary condition.

According to some embodiments, the sensor device includes an image sensor.

According to some embodiments, the image sensor is selected from the group consisting of a CMOS image sensor and a CCD image sensor.

According to some embodiments, the image sensor is selected from the group consisting of a thermal sensor, an IR sensor, a visible light sensor, and a UV sensor.

According to some embodiments, the array of photodetectors is configured to sense light of a wavelength between 280 nm to 4500 nm.

According to some embodiments, the array of photodetectors is configured to sense light of a wavelength between 280 nm to 3800 nm.

According to some embodiments, the optical sensor device further comprises a light source for transmitting a spectrum of light to external tissue (for example, skin) of said subject.

According to some embodiments, the optical sensor device further comprises a light source for transmitting a spectrum of light to internal tissue (for example, blood tissue and/or endothelial tissue) of said subject.

Non-limiting examples of light sources include but are not limited to natural sun light and/or artificial light sources for emitting a continuous and/or discontinuous spectrum of light such as white light sources, broad spectrum light sources (filtered and/or unfiltered), visual light, near IR light, IR light, above IR light, tungsten lamp light sources, an ultraviolet light source, and a gas light source (for example, a fluorescent light source).

According to some embodiments, the optical sensor device further comprises an alarm device, for indicating when a measured value indicative of said at least one said concentration deviates from an expected value of said local concentration.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide an image processing device for obtaining a chemical concentration in or on a mammalian subject said image processing device comprising:
  a) an image receiving unit for receiving a still or video electronic image of a first tissue of the mammalian subject; and
  b) an image processing unit for electronically processing said image and generating output indicative of a concentration of a substance within or on the mammalian subject.

According to some embodiments, the mammalian subject is a human subject.

According to some embodiments, the chemical concentration is selected from the group consisting of a concentration of a molecule and a chemical saturation.

According to some embodiments, the chemical concentration is a local concentration.

According to some embodiments, the image receiving unit includes a non-volatile memory device.

According to some embodiments, the image receiving unit is configured to receive said electronic image from a non-volatile memory device.

According to some embodiments, the processing unit is operative to generate output indicative of said local concentration of said substance within a second tissue of the mammalian subject.

According to some embodiments, tissue selected from the group consisting of a first tissue and a second tissue is selected from the group consisting of soft tissue, hard tissue, skin, surface tissue, outer tissue, internal tissue, a membrane, fetal tissue and endothelial tissue.

According to some embodiments, the processing unit is configured to generate output indicative a parameter selected from the group consisting of a glucose level, a pH level, a $CO_2$ level, an oxygen level, an oxygen saturation level, red cells concentration, a $CO_2$ saturation level, a bilirubin level, a skin saturation level, a concentration or saturation of salt, a concentration of an oily substance, and a urea nitrogen level.

According to some embodiments, the processing unit is configured to provide skin risk diagnostic.

According to some embodiments, the skin risk diagnostic is pigment biophysical diagnostic over and under the skin surface for suggesting for example pigment reduction treatment.

According to some embodiments, a risk diagnostic is a temporarily risk factor for exposing the skin to a light and heat such as direct and/or non direct sun rays for suggesting for example an appropriate sun protection.

According to some embodiments, the processing unit is operative to generate output indicative of a said concentration within bodily fluid of the mammalian subject.

According to some embodiments, the bodily fluid is selected from the group consisting of blood and sweat.

According to some embodiments, the processing unit is operative to generate output indicative of a said concentration within a circulatory system of the mammalian subject.

According to some embodiments, the processing unit is operative to generate output indicative of said a concentration within a blood vessel of said mammalian subject.

According to some embodiments, the processing unit is operative to generate output indicative of a said local concentration within a capillary of said mammalian subject.

According to some embodiments, the substance is dissolved or partially dissolved or suspended (i.e. blood cells) within a bodily fluid within the mammalian subject.

According to some embodiments, the optical sensor device further comprises a light source for transmitting a spectrum of light to and/or through said internal endothelial tissue of said subject.

According to some embodiments, the dissolved or partially dissolved substance is an ion.

According to some embodiments, the processing unit is operative to generate output indicative of pH.

According to some embodiments, the substance is a pigment.

According to some embodiments, the substance is a waste product.

According to some embodiments, the substance is a polymer.

According to some embodiments, the substance is a complexed polymer.

According to some embodiments, the substance is a biopolymer.

According to some embodiments, the substance is a protein.

According to some embodiments, the substance is a complexed protein.

According to some embodiments, the complexed protein is selected from the group consisting of a hemoglobin-oxygen complex and a hemoglobin-carbon dioxide complex.

According to some embodiments, the substance is a saccharide.

According to some embodiments, the saccharide is glucose.

According to some embodiments, the local concentration of said substance is indicative of a physiological condition in the subject selected from the group consisting of a condition of an internal organ (for example, kidney, liver, and/or heart, etc) condition of the liver, a condition of the kidney (for example, kidney failure, or a condition that is a precursor to kidney failure), a condition of the heart (for example, heart failure or a condition that is a precursor to heart failure), a pulmonary condition (for example, a breathing condition), cancer, a skin cancer, a blood cancer, a nutritional deficiency, a loss of blood, a malignant condition of bone marrow, dehydration, a cardiovascular condition, a physiological condition of a muscle, a presence of a microbe, a presence of an infectious microbe, an autoimmune condition, a presence of a fungus, and a pulmonary condition.

According to some embodiments, the electronic image is selected from the group consisting of a thermal image, an IR image, a visible light image, and a UV image.

According to some embodiments, the optical sensor array generates the electronic images and further comprises an alarm device, for indicating when a measured value indicative of said at least one said concentration deviates from an expected value of said local concentration.

According to some embodiments, the electronic image is observed by an optical sensor array sensitive to continues and discontinues spectrum of various light source transverse or reflected by the object or the combination thereof.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing and accessing look-up tables, computing an auto correlation, effecting a noise reduction, effecting functional ratio computation, computing and accessing look-up tables, effecting spatial and temporal derivative operation and effecting an iterative computation.

Some embodiments of the present invention provide computer-readable storage medium containing instruction data for obtaining a chemical concentration in or on a mammalian subject the instruction data comprising the instructions of:

a) processing a still or video electronic image of a first tissue of the mammalian subject; and b) generating from said processed image output indicative of concentration of a substance within or on the mammalian subject.

According to some embodiments, the mammalian subject is a human subject.

According to some embodiments, the chemical concentration is selected from the group consisting of a concentration of a molecule and a chemical saturation.

According to some embodiments, the chemical concentration is a local concentration of a chemical reaction or of a substance.

According to some embodiments a substance concentration is a number of red cells in a unit volume such as in a cubic millimeter. According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide a method of measuring a chemical concentration in or on a mammalian subject the method comprising:
 a) providing a still or video electronic image of a first tissue of the mammalian subject; and
 b) electronically processing said image to generate output indicative of a concentration of a substance within or on the mammalian subject.

According to some embodiments, the mammalian subject is a human subject.

According to some embodiments, the chemical concentration is selected from the group consisting of a concentration of a molecule and a chemical saturation.

According to some embodiments, the chemical concentration is a local concentration.

According to some embodiments, the processing includes processing said electronic image in a way that is insensitive to the race of the mammalian subject.

According to some embodiments, the step of providing includes receiving said image from a non-volatile memory device.

According to some embodiments, the step of providing includes obtaining said electronic image from a physical print image.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide an optical sensor device for detecting a chemical concentration in or on a food item the device comprising:
 a) an array of photodetectors, each photodetector configured to detect a spectrum of light, said array for receiving light reflected from and/or traversing a food item selected from the group consisting of food tissue, a dairy product, a beverage derived from food tissue, and a consumable alcoholic beverage and for producing an electric signal; and
 b) a processing unit adapted to receive and electronically process said electric signal to generate output indicative of a concentration of a substance within or on the food item.

According to some embodiments, each photodetector is configured to detect a continuous or discontinuous spectrum of light.

According to some embodiments, the chemical concentration is selected from the group consisting of a concentration of a molecule and a chemical saturation.

According to some embodiments, the chemical concentration is a local concentration.

According to some embodiments, the beverage is a beverage including fruit juice.

According to some embodiments, the dairy product is selected from the group consisting of a cheese, milk and a yoghurt.

According to some embodiments, the food tissue is selected from the group consisting of a fruit, a baked product, a bread, a cake, a product including sourdough, an edible plant, a vegetable, a leafy vegetable, a plant root, a soy product, dead animal tissue, meat, fish and eggs.

According to some embodiments, the consumable alcoholic beverage is selected from the group consisting of wine, beer, hard liquor, whiskey, rum, a beverage derived from hops, a malt beverage, and a fermented beverage.

According to some embodiments, the concentration is selected from the group consisting of a concentration of anthocyanins, a concentration of an antioxidant, a concentration of a plant pigment, an animal pigment, a concentration of an anti-inflammatory agent, and a concentration of a flavonoid, a concentration of myoglobin, a concentration of metmyoglobin, and a concentration of a protein.

According to some embodiments, the food tissue is a perishable item.

According to some embodiments, the concentration is indicative of a process selected from the group consisting of a cooking and a spoilage.

According to some embodiments, the concentration is indicative of a process selected from the group consisting of a spoilage of meat or fish or eggs, a spoilage of a dairy product, and a cooking of meat or fish or eggs.

According to some embodiments, the concentration is indicative of a grape ripeness.

According to some embodiments, the concentration is selected from a group consisting of environmental substance chemical markers.

According to some embodiments, the concentration is selected from a group consisting of environmental topological structure of liquid e.g. water, Sea water, river water, lake water, drinking water and substance such as metal, wood, gold, silver and gas such as air pollution.

According to some embodiments, the processing includes computing a parameter to adjust for ambient light.

According to some embodiments, the includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide an optical sensor device for detecting a chemical concentration in or on a liquid the device comprising:
 a) an array of photodetectors, each photodetector configured to detect a spectrum of light, said array for receiving light reflected from and/or traversing a liquid and for producing an electric signal; and b) a processing unit adapted to receive and electronically process said electric signal to generate output indicative of a concentration of a substance within or on the liquid.

According to some embodiments, each photodetector is configured to detect a continuous or discontinuous spectrum of light.

According to some embodiments, the liquid is an organic liquid.

According to some embodiments, the liquid is an aqueous solution.

According to some embodiments, the substance is selected from the group consisting of an organic substance, and a biological substance.

According to some embodiments, the an item selected from the group consisting of the liquid and the substance is derived from a petrochemical.

According to some embodiments, the an item selected from the group consisting of the liquid and the substance is toxic.

According to some embodiments, the processing includes generating an electronic image.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide an image processing device for obtaining a chemical concentration in or on a food item said image processing device comprising:

a) an image receiving unit for receiving a still or video electronic image of a food item selected from the group consisting of food tissue, a dairy product, a beverage derived from food tissue, and a consumable alcoholic beverage; and b) an image processing unit for electronically processing said image and generating output indicative of a concentration of a substance within or on the food item.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide an image processing device for obtaining a chemical concentration in or on a liquid said image processing device comprising:

a) an image receiving unit for receiving a still or video electronic image of a liquid; and b) an image processing unit for electronically processing said image and generating output indicative of a concentration of a substance within or on the liquid.

According to some embodiments, the liquid is an organic liquid.

According to some embodiments, the liquid is an aqueous solution.

According to some embodiments, the substance is selected from the group consisting of an organic substance, and a biological substance.

According to some embodiments an item selected from the group consisting of the liquid and the substance is derived from a petrochemical.

According to some embodiments, an item selected from the group consisting of the liquid and the substance is toxic.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide a computer-readable storage medium containing instruction data for obtaining a chemical concentration in or on a food item the instruction data comprising the instructions of:

a) processing a still or video electronic image of a food item selected from the group consisting of food tissue, a dairy product, a beverage derived from food tissue, and a consumable alcoholic beverage; and b) generating from said processed image output indicative of concentration of a substance within or on the food item selected from the group consisting of food tissue, a dairy product, a beverage derived from food tissue, and a consumable alcoholic beverage.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide computer-readable storage medium containing instruction data for obtaining a chemical concentration in or on a liquid the instruction data comprising the instructions of:
a) processing a still or video electronic image of a liquid; and
b) generating from said processed image output indicative of concentration of a substance within or on the liquid.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide method of measuring a chemical concentration in or on a food item the method comprising:
a) providing a still or video electronic image of a food item selected from the group consisting of food tissue, a dairy product, a beverage derived from food tissue, and a consumable alcoholic beverage; and
b) electronically processing said image to generate output indicative of a concentration of a substance within or on the food item.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide a method of measuring a chemical concentration in or on a liquid the method comprising:
a) providing a still or video electronic image of a liquid; and
b) electronically processing said image to generate output indicative of a concentration of a substance within or on the liquid.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide an optical sensor device for detecting biophysical information about a mammalian subject the device comprising:
a) an array of photodetectors, each photodetector configured to detect a spectrum of light, said array for receiving light reflected from and/or traversing a first tissue of the mammalian subject and for producing an electric signal; and
b) a processing unit adapted to receive and electronically process said electric signal to generate output indicative of a biophysical parameter of the mammalian subject.

According to some embodiments, each photodetector is configured to detect a continuous or discontinuous spectrum of light.

According to some embodiments, the mammalian subject is a human subject.

According to some embodiments, the biophysical parameter is a temporal parameter.

According to some embodiments, the biophysical parameter is selected from the group consisting of a heartbeat, a pulse transition time (PTT), stroke volume variation, a vessel deformation parameter, and a blood pressure.

According to some embodiments, the biophysical parameter is a temperature at a location within the subject.

According to some embodiments, the biophysical parameter is a temperature fluctuation at a location within the subject.

According to some embodiments, the biophysical parameter is a temperature fluctuation on or in the skin of the subject.

According to some embodiments, the biophysical parameter is selected from the group consisting of a systolic pressure and a diastolic pressure.

According to some embodiments, the biophysical parameter is related to a heartbeat of the mammalian subject.

According to some embodiments, the processing unit is configured to generate output indicative a parameter selected from the group consisting of a glucose level, a pH level, a $CO_2$ level, an oxygen level, an oxygen saturation level, red cells concentration, a $CO_2$ saturation level, a bilirubin level, a skin saturation level, a concentration or saturation of salt, a concentration of an oily substance, and a urea nitrogen level.

According to some embodiments, the biophysical parameter is indicative of physiological condition selected from the group consisting a physiological condition of the skin, a cardiovascular condition, a pulmonary condition, a physiological condition of an internal organ, a physiological condition of an organ associated with the digestive system, a physiological condition of the kidneys, a physiological condition of the liver, and a physiological condition of the blood.

According to some embodiments, the processing unit is operative to generate output indicative of a biophysical parameter of a bodily fluid of the mammalian subject.

According to some embodiments, the bodily fluid is selected from the group consisting of blood and sweat.

According to some embodiments, the processing unit is operative to generate output indicative of a biophysical parameter of a circulatory system of the mammalian subject.

According to some embodiments, the biophysical parameter is indicative of a physiological condition in the subject selected from the group consisting of a condition of the liver, a physiological condition of the skin, a physiological condition of an internal organ, a physiological condition of an organ associated with the digestive system, a condition of the kidney, a physiological condition of the blood, a condition of the liver, a cancer, a skin cancer, a blood cancer, a nutritional deficiency, a loss of blood, a malignant condition of bone marrow, dehydration, a cardiovascular condition, a physiological condition of a muscle, a presence of a microbe, a presence of an infectious microbe, an autoimmune condition, a presence of a fungus, and a pulmonary condition.

According to some embodiments, the electronic image is selected from the group consisting of a thermal image, an IR image, a visible light image, and a UV image.

According to some embodiments, the biophysical parameter is selected from the group consisting of oil moisture content of skin, skin dryness, skin absorption potential, skin pigmentation, red cells concentration, blood pressure, skin pH, skin saltiness level, a condition related to skin saturation, a condition related to skin vitality, a condition related to sweat, a condition related to skin deformation, a condition related to local skin deformation, and a condition related to skin wrinkles. According to some embodiments, "skin absorption potential" are local levels over different skin areas where the potential to absorb certain substance such as water or moisture is relatively high or low in different skin areas.

According to some embodiments, the biophysical parameter is selected from the group consisting of an O2 blood saturation level, a blood glucose level, a blood pH level, Red Cells Concentration, a blood $CO_2$ level, and a blood urea nitrogen level.

According to some embodiments, the device further comprises an alarm device, for indicating when a measured value indicative of said a biophysical parameter deviates from an expected value of a said biophysical parameter.

According to some embodiments, the sensor device includes an image sensor.

According to some embodiments, the image sensor is selected from the group consisting of a CMOS image sensor and a CCD image sensor.

According to some embodiments, the image sensor is selected from the group consisting of a thermal sensor, an IR sensor, a visible light sensor, and a UV sensor.

According to some embodiments, the array of photodetectors is configured to sense light of a wavelength between 280 nm to 4500 nm.

According to some embodiments, the array of photodetectors is configured to sense light of a wavelength between 280 nm to 3800 nm.

According to some embodiments, the device further comprises a light source for transmitting a spectrum of light to said tissue of said subject.

According to some embodiments, the light source is selected from the group consisting of a natural light source (sun light) or artificial light source for emitting a continuous or discontinuous spectrum of light.

According to some embodiments, the biophysical parameter is a malignant physiological condition.

According to some embodiments, the malignant condition is selected from the group consisting of an autoimmune disorder, psoriasis, an allergic condition, an inflammatory condition, a proliferative disorder, a cancer, a melanoma, a presence of an infectious microbe a fungal infection, a cardiovascular condition, a malady of an internal organ.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide an image processing device for obtaining biophysical information about a mammalian subject said image processing device comprising:
 a) an image receiving unit for receiving a still or video electronic image of a first tissue of the mammalian subject; and
 b) an image processing unit for electronically processing said image and generating output indicative of a biophysical parameter of the mammalian subject.

192 According to some embodiments, the mammalian subject is a human subject.

According to some embodiments, the biophysical parameter is a temporal parameter.

According to some embodiments, the biophysical parameter is selected from the group consisting of a heartbeat, a pulse transition time (PTT), stroke volume variation, vessel deformation and a blood pressure.

According to some embodiments, the biophysical parameter is a temperature at a location within the subject.

According to some embodiments, the said biophysical parameter is a temperature fluctuation at a location within the subject.

According to some embodiments, the biophysical parameter is a temperature fluctuation on or in the skin of the subject.

According to some embodiments, the image receiving unit includes a non-volatile memory device.

According to some embodiments, the image receiving unit is configured to receive said electronic image from a non-volatile memory device.

According to some embodiments, the processing unit is configured to generate output indicative a parameter selected from the group consisting of a glucose level, a pH level, a CO2 level, an oxygen level, an oxygen saturation level, red cells concentration, a CO2 saturation level, a bilirubin level, a skin saturation level, a concentration or saturation of salt, a concentration of an oily substance, a concentration of red cells, and a urea nitrogen level.

According to some embodiments, the biophysical parameter is indicative of physiological condition selected from the group consisting a physiological condition of the skin, a cardiovascular condition, a pulmonary condition, a physiological condition of an internal organ, a physiological condition of an organ associated with the digestive system, a physiological condition of the kidneys, a physiological condition of the liver, and a physiological condition of the blood.

According to some embodiments, the processing unit is operative to generate output indicative of a biophysical parameter of a bodily fluid of the mammalian subject.

According to some embodiments, the bodily fluid is selected from the group consisting of blood and sweat.

According to some embodiments, the processing unit is operative to generate output indicative of a biophysical parameter of a circulatory system of the mammalian subject.

According to some embodiments, the biophysical parameter is indicative of a physiological condition in the subject selected from the group consisting of a condition of the liver, a physiological condition of the skin, a physiological condition of an internal organ, a physiological condition of an organ associated with the digestive system, a condition of the kidney, a physiological condition of the blood, a condition of the liver, a cancer, a skin cancer, a blood cancer, a nutritional deficiency, a loss of blood, a malignant condition of bone marrow, dehydration, a cardiovascular condition, a physiological condition of a muscle, a presence of a microbe, a presence of an infectious microbe, an autoimmune condition, a presence of a fungus, and a pulmonary condition.

According to some embodiments, the electronic image is selected from the group consisting of a thermal image, an IR image, a visible light image, and a UV image.

According to some embodiments, the biophysical parameter is selected from the group consisting of oil moisture content of skin, skin dryness, skin absorption potential, skin pigmentation, red cells concentration, skin pH, skin saltiness level, a condition related to skin saturation, a condition related to skin vitality, a condition related to sweat, and a condition related to skin wrinkles.

According to some embodiments, the biophysical parameter is selected from the group consisting of an O2 blood saturation level, a blood glucose level, a blood pH level, Red Cells Concentration, a blood CO2 level, and a blood urea nitrogen level.

According to some embodiments, the device further comprises: c) an alarm device, for indicating when a measured value indicative of said a biophysical parameter deviates from an expected value of a said biophysical parameter.

According to some embodiments, the biophysical parameter is selected from the group consisting of a systolic pressure and a diastolic pressure.

According to some embodiments, the biophysical parameter is related to a heartbeat of the mammalian subject.

According to some embodiments, the biophysical parameter is a malignant physiological condition.

According to some embodiments, the malignant condition is selected from the group consisting of an autoimmune disorder, psoriasis, an allergic condition, an inflammatory condition, a proliferative disorder, a cancer, a melanoma, a presence of an infectious microbe a fungal infection, a cardiovascular condition, a malady of an internal organ.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide a computer-readable storage medium containing instruction data for obtaining biophysical information about a mammalian subject the instruction data comprising the instructions of:

a) processing a still or video electronic image of a first tissue of the mammalian subject; and b) generating from said processed image output indicative of biophysical condition within or on the mammalian subject.

According to some embodiments, the said processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide a method of measuring biophysical information about a mammalian subject the method comprising:

a) providing a still or video electronic image of a first tissue of the mammalian subject; and
b) electronically processing said image to generate output indicative of a biophysical condition of the mammalian subject.

According to some embodiments, the mammalian subject is a human subject.

According to some embodiments, the processing includes processing said electronic image in a way that is insensitive to the race of the mammalian subject.

According to some embodiments, the step of providing includes receiving said image from a non-volatile memory device.

According to some embodiments, the step of providing includes obtaining said electronic image from a physical print image.

According to some embodiments, the stage of providing includes receiving light within a photodetector within a housing, and said housing is a distance from said first tissue.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide an optical sensor device for detecting biophysical information about a food item the device comprising:
a) an array of photodetectors, each photodetector configured to detect a spectrum of light, said array for receiving light reflected from and/or traversing a food item selected from the group consisting of food tissue, a dairy product, a beverage derived from food tissue, and a consumable alcoholic beverage and for producing an electric signal; and
b) a processing unit adapted to receive and electronically process said electric signal to generate output indicative of a biophysical parameter of the food item selected from the group consisting of food tissue, a dairy product, a beverage derived from food tissue, and a consumable alcoholic beverage.

According to some embodiments, each photodetector is configured to detect a continuous or discontinuous spectrum of light.

According to some embodiments, the beverage is a beverage including fruit juice.

According to some embodiments, the dairy product is selected from the group consisting of a cheese, milk and a yoghurt.

According to some embodiments, the food tissue is selected from the group consisting of a fruit, an edible plant, a vegetable, a leafy vegetable, a plant root, a soy product, dead animal tissue, meat, fish and egs.

According to some embodiments, the consumable alcoholic beverage is selected from the group consisting of wine, beer, hard liquor, whiskey, rum, a beverage derived from hops, a malt beverage, and a fermented beverage.

According to some embodiments, the biophysical parameter is selected from the group consisting of a concentration of anthocyanins, a concentration of an antioxidant, a concentration of a plant pigment, an animal pigment, a concentration of an anti-inflammatory agent, and a concentration of a flavonoid, a concentration of myoglobin, a concentration of metmyoglobin, and a concentration of a protein.

According to some embodiments, the food tissue is a perishable item.

According to some embodiments, the biophysical parameter is indicative of a process selected from the group consisting of a cooking and a spoilage.

According to some embodiments, the biophysical parameter is indicative of a process selected from the group consisting of a spoilage of meat or fish or eggs, a spoilage of a dairy product, and a cooking of meat or fish or eggs.

According to some embodiments, the biophysical parameter is indicative of a grape ripeness.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide an optical sensor device for detecting biophysical information about a liquid the device comprising:
a) an array of photodetectors, each photodetector configured to detect a spectrum of light, said array for receiving light reflected from and/or traversing a liquid and for producing an electric signal; and
b) a processing unit adapted to receive and electronically process said electric signal to generate output indicative of a biophysical condition of the liquid.

According to some embodiments, each photodetector is configured to detect a continuous or discontinuous spectrum of light.

According to some embodiments, the processing includes computing a parameter to adjust for ambient light.

According to some embodiments, the said processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide an image processing device for obtaining biophysical information about a food item said image processing device comprising:
 a) an image receiving unit for receiving a still or video electronic image of a food item selected from the group consisting of food tissue, a dairy product, a beverage derived from food tissue, and a consumable alcoholic beverage; and
 b) an image processing unit for electronically processing said image and generating output indicative of a biophysical condition of the food item selected from the group consisting of food tissue, a dairy product, a beverage derived from food tissue, and a consumable alcoholic beverage.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide an image processing device for obtaining biophysical information about a liquid said image processing device comprising:
 a) an image receiving unit for receiving a still or video electronic image of a liquid; and
 b) an image processing unit for electronically processing said image and generating output indicative of a biophysical condition of the liquid.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

According to some embodiments, at least one said photodetector of any optical sensor disclosed herein is selected from the group consisting of a photodetector configured to detect light of wavelength less than 421 nm, a photodetector configured to detect light of wavelength greater than 423 nm and less than 452 nm, a photodetector configured to detect light of wavelength greater than 454 nm and less than 498 nm, a photodetector configured to detect light of wavelength greater than 500 nm and less than 528 nm, a photodetector configured to detect light of wavelength greater than 530 nm and less than 545 nm, a photodetector configured to detect light of wavelength greater than 547 nm and less than 568 nm, and a photodetector configured to detect light of wavelength greater than 570 nm and less than 583 nm, and a photodetector configured to detect light of wavelength greater than 585 nm and less than 600 nm.

Some embodiments of the present invention provide a computer-readable storage medium containing instruction data for obtaining biophysical information about a food item the instruction data comprising the instructions of:
 a) processing a still or video electronic image of a food item selected from the group consisting of food tissue, a dairy product, a beverage derived from food tissue, and a consumable alcoholic beverage; and
 b) generating from said processed image output indicative of biophysical condition within or on the food item selected from the group consisting of food tissue, a dairy product, a beverage derived from food tissue, and a consumable alcoholic beverage.

According to some embodiments, the processing includes computing a parameter to adjust for ambient light.

According to some embodiments, the said processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide a computer-readable storage medium containing instruction data for obtaining biophysical information about a liquid the instruction data comprising the instructions of:
 a) processing a still or video electronic image of a liquid; and
 b) generating from said processed image output indicative of biophysical condition within or on the liquid.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

It is now disclosed for the first time a method of measuring biophysical information about a food item the method comprising:
a) providing a still or video electronic image of a food item selected from the group consisting of food tissue, a dairy product, a beverage derived from food tissue, and a consumable alcoholic beverage; and
b) electronically processing said image to generate output indicative of a biophysical condition of the food item selected from the group consisting of food tissue, a dairy product, a beverage derived from food tissue, and a consumable alcoholic beverage.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide a method of measuring biophysical information about a liquid the method comprising:
a) providing a still or video electronic image of a liquid; and
b) electronically processing said image to generate output indicative of a biophysical condition of the liquid.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide a optical sensor device for detecting physiological information about a mammalian subject the device comprising:
a) an array of photodetectors, each photodetector configured to detect a spectrum of light, said array for receiving light reflected from and/or traversing a first tissue of the mammalian subject and for producing an electric signal; and
b) a processing unit adapted to receive and electronically process said electric signal to generate output indicative of a physiological condition of the mammalian subject.

According to some embodiments, each photodetector is configured to detect a continuous or discontinuous spectrum of light.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide an image processing device for obtaining physiological information about a mammalian subject said image processing device comprising:
a) an image receiving unit for receiving a still or video electronic image of a first tissue of the mammalian subject; and
b) an image processing unit for electronically processing said image and generating output indicative of a physiological condition of the mammalian subject.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide a computer-readable storage medium containing instruction data for obtaining physiological information about a mammalian subject the instruction data comprising the instructions of:
 a) processing a still or video electronic image of a first tissue of the mammalian subject; and
 b) generating from said processed image output indicative of physiological condition within or on the mammalian subject.

According to some embodiments, the said processing includes computing a parameter to adjust for ambient light.

According to some embodiments, the said processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide a method of measuring physiological information about a mammalian subject the method comprising:
 a) providing a still or video electronic image of a first tissue of the mammalian subject; and
 b) electronically processing said image to generate output indicative of a physiological condition of the mammalian subject.

According to some embodiments, the mammalian subject is a human subject.

According to some embodiments, the processing includes processing said electronic image in a way that is insensitive to the race of the mammalian subject.

According to some embodiments, the step of providing includes receiving said image from a non-volatile memory device.

According to some embodiments, the step of providing includes obtaining said electronic image from a physical print image.

According to some embodiments, the stage of providing includes receiving light within a photodetector within a housing, and said housing is a distance from said first tissue.

According to some embodiments, the processing includes computing a parameter to adjust for ambient light.

According to some embodiments, the processing includes effecting a process selected from the group consisting of effecting a color coordinate transformation and effecting a noise reduction.

According to some embodiments, the processing includes computing a solution vector to a set of linear or non-linear equations, wherein said equations are selected from the group consisting of algebraic or functional equations, differential equations and partial differential equations.

According to some embodiments, the processing includes computing from said solution vector a desired parameter, wherein said computation of said desired parameter includes at least one process selected from the group consisting of computing a correlation, computing a cross correlation, computing an auto correlation, effecting a noise reduction, effecting functional ratio computation, computing and accessing look-up tables, effecting spatial and temporal derivative operation and effecting an iterative computation.

Some embodiments of the present invention provide a method of obtaining physiological information about a mammalian subject, the method comprising:
 a) providing an array of photodetectors within a housing;
 b) receiving light reflected from and/or traversing soft tissue of the subject into said array of photodetectors to produce an electrical signal wherein said housing is disposed at a distance from said subject; and
 c) processing said electrical signal to generate an output indicative of a parameter selected from the group consisting of a concentration of a substance and a biophysical parameter of the subject.

Some embodiments of the present invention provide a polygraph device for determining a stage of agitation of a subject comprising:
 a) an image receiving unit for receiving a series of video digital images of a subject over a period of time;
 b) an image processing unit for generating from said video digital images output indicative of a physiological condition of the subject over said period of time; and
 c) a physiological condition variation detection module, for examining said output and determining if physiological condition variation is indicative that the subject is in a state of agitation.

Some embodiments of the present invention provide a polygraph device for determining a stage of agitation of a subject comprising:
 a) an image receiving unit for receiving a video digital image of a subject;
 b) an image processing unit for generating from said video digital image output indicative of a physiological condition of the subject; and
 c) a physiological condition comparison module, for determining when said output indicative of said physiological condition deviates from a value associated with a relaxed person.

Some embodiments of the present invention provide a device for determining a cosmetic regimen of treatment, the device comprising:
 a) an image receiving unit for receiving a video digital image of a subject;
 b) an image processing unit for generating from said video digital image output indicative of a physiological condition of the skin of said subject; and
 c) a treatment output module for receiving said generated output and generating output descriptive of a cosmetic regimen for improving said physiological condition of said skin of said subject.

According to some embodiments, the physiological condition is selected from the group consisting of a skin pH, a skin moisture and a skin dryness.

Some embodiments of the present invention provide a device for detecting a pH of wine, the device comprising:

a) an image receiving unit for receiving a still or video electronic image of wine;
b) an image processing unit for processing said electronic images and generating output indicative of a pH of said wine.

According to some embodiments, the electronic image is a video or still image of wine within a vessel.

According to some embodiments, the vessel is sealed.

According to some embodiments, the vessel is transparent, and said processing includes processing the video image in a way that is insensitive to the presence of said vessel.

Some embodiments of the present invention provide a method of determining of a life status of a mammalian subject the method comprising:
a) obtaining a still or video electronic image of the subject;
b) electronically processing said image to generate output indicative of a life parameter selected from the group consisting of a biophysical parameter and a concentration of a substance within or on the mammalian subject;
c) deducing the life status from said output.

According to some embodiments, the life status is selected from the group consisting of whether the mammalian subject is alive or dead and a time of death.

Some embodiments of the present invention provide a device for determining of a life status of a mammalian subject the device comprising:
a) an image receiving unit for receiving a still or video electronic image of a first tissue of the mammalian subject;
b) an image processing unit for electronically processing said image and generating output indicative of a life parameter selected from the group consisting of a concentration of a substance within or on the mammalian subject and a biophysical parameter; and
c) a life status unit for determining the life status from said output.

According to some embodiments, the life status is selected from the group consisting of whether the mammalian subject is alive or dead and a time of death.

Some embodiments of the present invention provide an optical sensor device for detecting a concentration of at least one substance in or on a mammalian subject the device comprising:
a) an array of photodetectors, each photodetector configured to detect a spectrum of light, said array for receiving light reflected from and/or traversing a first tissue of the mammalian subject and for producing an electric signal; and
b) a processing unit adapted to receive and electronically process said electric signal to generate output indicative of at least one of a concentration (i.e. at a given location) and a concentration profile of at least one substance (for example, a chemical concentration) within or on the mammalian subject or a region thereof.

According to some embodiments, the device is part of a system including a natural light source (sun light) or artificial light sources.

According to some embodiments, the concentration profile is selected from the group consisting of a spatial concentration profile (obtained, for example, by calculating concentration on a pixel by pixel basis, with a different concentration calculated per pixel or per group of pixels) and a temporal concentration profile (for example, by calculating concentration of a plurality of times to derive the temporal concentration profile).

According to some embodiments, the concentration of a substance is a chemical concentration and said processing unit is adapted to generate output indicative of said chemical concentration.

According to some embodiments, the concentration of said substance is a concentration beneath a surface of said first tissue.

According to some embodiments, the concentration of said substance is a concentration in a localized region of said first tissue.

According to some embodiments, the concentration of said substance is a concentration in a layer of said first tissue.

According to some embodiments, the concentration of said substance is a concentration in a sub-tissue of said first tissue.

According to some embodiments, the concentration of a substance is a tissue surface smoothness indicative of the undersurface substance concentration such as Collagen.

According to some embodiments, the electronic processing includes computing a smoothness function.

According to some embodiments, the i) said array of photodetectors is adapted to receive light including light reflected from said first tissue and to produce said electric signal in accordance with said received reflected light; and ii) said processing unit is adapted to generate said indicative output in accordance with said electric signal derived from said reflected light.

According to some embodiments, the i) said array of photodetectors is adapted to receive light including light traversing said first tissue and to produce said electric signal in accordance with said received traversing light; ii) said processing unit is adapted to generate said indicative output in accordance with said electric signal derived from said traversing light.

According to some embodiments, the tissue includes at least one of a matrix (for example, jelly-like tissue) and a mass of solid tissue (for example, a unified solid tissue).

According to some embodiments, said tissue includes tissue elements suspended in a fluid.

According to some embodiments, said tissue includes tissue elements suspended in a bodily fluid.

According to some embodiments, said tissue includes blood tissue (for example, blood cells suspended in plasma).

It is now disclosed for the first time an optical sensor device for detecting a concentration of at least one substance in or on a mammalian subject the device comprising (a) an array of photodetectors for receiving light reflected from and/or traversing a tissue of the mammalian subject and for producing an electric signal; and (b) a processing unit adapted to receive and electronically process said electric signal to generate output indicative of at least one of a concentration and a concentration profile of at least one substance within or on the mammalian subject or a region thereof.

According to some embodiments, said substance is other than a oxygen-containing gas.

According to some embodiments, said substance is other than a gas dissolved in the blood.

It is now disclosed for the first time a method for detecting a concentration of at least one substance in or on a mammalian subject the device comprising:
a) detecting light reflected from and/or traversing a tissue of the mammalian subject to produce an electric signal;
b) electronically processing said electric signal to generate output indicative of at least one of a concentration and a concentration profile of at least one substance within or on the mammalian subject or a region thereof.

According to some embodiments, said substance is other than an oxygen-containing gas.

According to some embodiments, said substance is other than a gas dissolved in the blood.

According to some embodiments, said substance is a collagen.

It is now disclosed for the first time a method for measuring efficacy of a medical treatment procedure of soft tissue, the method comprising:
a) subjecting the patient to the medical treatment procedure at least once;
b) after each said medical procedure, measuring at least one of a concentration and a concentration profile of at least one substance on, in or below a surface of the soft-tissue by generating an electrical signal in accordance with detected light reflected from and/or traversing a tissue of the mammalian subject to produce an electric signal;
c) Deriving from at least one respective said measured concentration or concentration profile a parameter indicative of the efficacy of said medical treatment procedure.

According to some embodiments, said substance is collagen.

According to some embodiments, said patient is subjected to said medical treatment a plurality of times to produce a plurality of respective measurements, and said parameter indicative of said efficacy is derived from said plurality of respective measurements.

According to some embodiments, said deriving of said parameter indicative of the efficacy includes computing a trend function of said respective measurements.

According to some embodiments, each of said plurality of times are separated by at least one hour.

It is now disclosed for the first time an optical sensor device for detecting a concentration and/or a concentration profile of a collagen in at a location or region of a soft tissue of mammalian subject the device comprising:
a) an array of photodetectors for receiving light reflected from and/or traversing the soft tissue of the mammalian subject and for producing an electric signal; and
b) a processing unit adapted to receive and electronically process said electric signal to generate output indicative of at least one of a concentration and a concentration profile of the collagen at or in the location or region of the soft tissue of the mammalian subject.

It is now disclosed for the first time an optical sensor device for detecting a concentration and/or a concentration profile of a collagen in at a location or region of a soft tissue of mammalian subject the device comprising:
a) an array of photodetectors for receiving light reflected from and/or traversing the soft tissue of the mammalian subject and for producing an electric signal; and
b) a processing unit adapted to receive and electronically process said electric signal to generate output indicative of at least one of a concentration and a concentration profile of the collagen at or in the location or region of the soft tissue of the mammalian subject.

It is now disclosed for the first time an method of measuring a chemical concentration in or on a substance the method comprising:
a) providing a still or video electronic image of a liquid; and
b) electronically processing said image to generate output indicative of a concentration of a substance within or on the substance.

According to some embodiments, said substance is selected form the group consisting of a liquid, a gas, a solid and a mixture of any combination thereof.

According to some embodiments, said substance is selected form the group consisting of water, Sea water, river water, lake water, and drinking water.

According to some embodiments, said substance is selected form the group consisting of as metal, wood, gold, and silver.

According to some embodiments, said chemical concentration is a concentration of environmental substance chemical markers.

It is now disclosed for the first time a method for detecting a chemical concentration in or on a substance the method comprising:
a) detecting light reflected from and/or traversing a tissue of substance to produce an electric signal;
b) electronically processing said electric signal to generate output indicative of at least one of a chemical concentration and a chemical concentration profile in or on the substance.

According to some embodiments, the first tissue is selected from the group consisting of soft tissue, hard tissue, skin tissue, surface tissue, outer tissue, internal tissue, a membrane, fetal tissue, liquid tissue, and endothelial tissue.

According to some embodiments, processing unit is adapted to generate output indicative of a concentration of a substance having a characteristic dimension that is greater than 0.1 micron and less than 20 microns (for example, blood cells).

According to some embodiments, said processing unit is adapted to generate output indicative of a concentration of a substance having a characteristic dimension that is greater than 1 micron and less than 20 microns.

According to some embodiments, said processing unit is adapted to generate output indicative of a concentration of a substance having a characteristic dimension that is greater than 1 micron and less than 10 microns (for example, blood cells).

According to some embodiments, said processing unit is adapted to generate output indicative of a concentration of at least one type of cell.

According to some embodiments, said processing unit is adapted to generate output indicative of a concentration of at least one type of blood cell (for example, red blood cells, white blood cells and the combination thereof).

According to some embodiments, said processing unit is adapted to generate output indicative of a concentration of a red blood cell The following examples are to be considered merely as illustrative and non-limiting in nature. It will be apparent to one skilled in the art to which the present invention pertains that many modifications, permutations, and variations may be made without departing from the scope of the invention.

Example 1

RBG Video Input

Let $R(t)$, $G(t)$ and $B(t)$ be the spatial temporal visible video RGB color space, and let $P_{ij}(R(t),G(t),B(t))=(R_{ij}(t),G_{ij}(t),B_{ij}(t))$ represent spatial temporal video pixel information. P is considered as the hybrid color pixel value observed by the eye from the red, green and blue pixel luminance information.

Usually video signal input is formatted as YCbCr and it is lineally related to the RGB space. If video input is in different color space (format) such as YUV, YCrCb, YIQ, HIQ, etc. there exists a linear or non linear transformation to transform between any color space and the RGB color space. Therefore, without reducing the generality of the presented image processing techniques, the techniques are presented in terms of a common spatial temporal RGB color space.

Although the aforementioned color space was presented in terms of luminance information from the visible spectrum, the present invention relates to method of and devices for processing luminance information from spectrum outside of the visible spectrum. Radiation of any wavelength is appropriate for the present invention. In some embodiments, radiation in a spectra from 200 nm to 4500 nm is detected and analyzed. In some embodiments, of wavelength less than 4000 nm is detected and analyzed.

Furthermore, it is noted that the examples presented herein relate to the specific case of three spectra with overlapping wavelengths, namely red, green and blue. In some embodiments, the color space includes only two wavelength ranges. In some embodiments, the color space includes three or more wavelength ranges.

Example 2

Preprocessing of Video Input

In some embodiments, it is useful to apply the presently disclosed algorithm to transformed color values rather than to directly sensed or recorded values in color space. Thus, optionally, the physically sensed or measured values are subjected to a transformation of the form $$R' = E_r(R, G, B, \overline{A_R})$$

$$G' = E_g(R, G, B, \overline{A_G})$$

$$B' = E_b(R, G, B, \overline{A_B}) \quad (2)$$

yielding R', G', B', which are defined as transformed values of measured R,G,B, and wherein $\overline{A_R}, \overline{A_G}, \overline{A_B}$ are free constants chosen by the skilled artisan.

The present inventor has found that the following exemplary color transformations are useful for the present invention:

$$R' = \frac{\overline{A_r} \cdot (R-B) \cdot R^2}{G \cdot B} \quad (3a)$$

$$G' = \frac{\overline{A_g} \cdot (R-G) \cdot G^2}{R \cdot B}$$

$$B' = \frac{\overline{A_b} \cdot (G-B) \cdot B^2}{G \cdot R}$$

$$R' = \frac{\overline{A_r} \cdot R^2}{G \cdot B} \quad (3b)$$

$$G' = \frac{\overline{A_g} \cdot G^2}{R \cdot B}$$

$$B' = \frac{\overline{A_b} \cdot B^2}{G \cdot R}$$

$$R' = \frac{\overline{A_r} \cdot R}{\text{sqrt}(R^2 + G^2 + B^2)} \quad (3c)$$

$$G' = \frac{\overline{A_g} \cdot G}{\text{sqrt}(R^2 + G^2 + B^2)}$$

$$B' = \frac{\overline{A_b} \cdot B}{\text{sqrt}(R^2 + G^2 + B^2)}$$

-continued $$R' = \frac{\overline{A_r} \cdot R}{(R + G + B)} \quad (3d)$$

$$G' = \frac{\overline{A_g} \cdot G}{(R + G + B)}$$

$$B' = \frac{\overline{A_b} \cdot B}{(R + G + B)}.$$

$$R' = \overline{A_r} \cdot R \quad (3e)$$

$$G' = \overline{A_g} \cdot G$$

$$B' = \overline{A_b} \cdot B$$

$$R' = R \quad (3f)$$

$$G' = G$$

$$B' = B.$$

The skilled artisan will appreciate that the specific transformation or transformations is chosen appropriately based upon the physical specifications of the camera or CCD used, the local lighting conditions, or other image parameters.

Both linear as well as nonlinear transformations including the identity transformation of the vector space RGB to a new vector space R'G'B' are appropriate. In some embodiments, it is preferred to apply an orthogonal process such as Karhunen-Loe've (KL) transformation of the RGB color vector into R'G'B' for achieving better color separation. Not wishing to be bound by any particular theory, it is noted that sometimes a color coordinate transformation is required in order to achieve better color separation and to achieve a lower sensitivity (i.e. more robust) to light fluctuations. Nevertheless, in some cases a pre color adjustment such as white and/or black balancing or general color balancing according to the current environment is required for better accurate and robust results. Such balancing can be done manually or automatically, and these techniques are well known in the art.

Furthermore, it is noted that for certain situations more than one transformation is equally appropriate, and more than one option can be chosen.

For the specific case described above, R, G and B represent the pixel value in the finite range [A . . . B] for A and B real numbers. Thus, without reducing the generality we have presented above few examples.

Example 3

A Set of Equations for Meta-Biophysical Parameters

In exemplary embodiments, the sought after physiological parameters or biophysical parameters or substance concentrations are obtained only after first obtaining values for a set of vectors of biophysical meta-parameters for a given time t, $\{\overline{C(t)}\} = \{(C_0^1(t), \ldots, C_0^1(t)), (C_1^1(t), \ldots, C_L^1(t)), (C_1^2(t), \ldots, C_L^2(t)), \ldots, (C(t)_L^N, \ldots, C((t)_L^N)\}$. It is noted that the notation $C_{ij}(t)$ will be used interchangeably with $C_i^j(t)$ One exemplary set of equations that is useful for obtaining values for this set of vectors of the unknown biophysical meta-parameters is given by:

$$F_{ij}(C_{ij}(t)) = G_{ij}(R', G', B') \begin{array}{l} i = 1, 2, \ldots L \\ j = 1, 2, \ldots N \end{array}. \quad (4)$$

In some embodiments, in order to solve for the unknown meta-biophysical parameters, (4) is supplemented by a boundary condition on $\{\overline{C(t)}\}$. Two exemplary boundary conditions:

$$\sum_{i=0}^{L} C_{ij}(t) = 1 \text{ for } j = 1, 2, \ldots N \tag{5a}$$

and $$\sum_{i=0}^{L} [C_{ij}(t)]^2 = 1 \text{ for } j = 1, 2, \ldots N \tag{5b}$$

An additional well known case is where the measure function is the identity i.e. m(C)=1 and the norm is Euclidian norm which transformed the set of parameters C onto the spherical unit ball $S^L$.

The skilled artisan will appreciate that other boundary conditions are appropriate for the present invention.

The present inventor has discovered that a judicious choice of transformation functions in (4) allows one to obtain a solution for the biophysical meta-parameters such that subsequently derived values for physiological parameters or biophysical parameters or concentrations give a good estimate of their true values.

It is noted that the set of equations specified in (4) is only one exemplary form of equations for obtaining values of biophysical meta-parameters. Thus, the set of equations enumerated in (4) is a particular case of the general set of equations denoted by:

$$F_{ij}(C_{ij}(t)) = G_{ij}(R', G', B', C_{ij}(t), \overline{D}, t) \begin{matrix} i = 1, 2, \ldots L \\ j = 1, 2, \ldots N \end{matrix} \tag{4'}$$

where the parameters vector is given by $\overline{D}=(D_1, \ldots, D_L)$.

Thus, any solution for biophysical meta-parameters obtained by using the more general set of equations (4') falls within the spirit and scope of the present invention.

Example 4

Choosing Appropriate Biophysical Transformation $F_{ij}$ Operators

One exemplary transformation $F_{ij}$ that the present inventor has found useful is:

$$F_{ij}(C_{ij}) = \frac{C_{0j}}{C_{0j} + C_{ij}} \tag{6}$$

We note that the function form provided by (6) is identical to the functional form appearing on the left hand side of 1 (a).

Example 5

Choosing Appropriate Color Space Transformations $G_{ij}$

The functions $G_{ij}$ define relationships between the unknown biophysical meta-parameters $\{\overline{C(t)}\}$ and the aggregate wavelength distributions within two or more wavelength ranges sensed by the camera image color sensor.

In some embodiments, the color space transformations are given as a permutation operators, i.e.

$$G_{ij}(R',G',B')=P_{ij}(R',G',B') \tag{7a}$$

The present inventor has found that in some embodiments the following permutations are useful:

$$P_1(R', G', B') = \frac{R'}{B'}$$
$$P_2(R', G', B') = \frac{G'}{R'}$$
$$P_3(R', G', B') = \frac{B'}{G'}$$
$$P_4(R', G', B') = \frac{R'}{G'} ,$$
$$P_5(R', G', B') = \frac{G'}{B'}$$
$$P_6(R', G', B') = \frac{B'}{R'}$$
$$\tag{7b}$$

Optionally, the permutations of 7(b) can be reduced into three major permutation $P_1$, $P_2$ and $P_2$.

Example 6

An Exemplary Solution for Biophysical Metaparameters

In Example 6, an exemplary solution is presented for the specific case of where L=6, N=1, $F_{ij}$ given by equation (6), boundary condition 5(b) is chosen. Adopting the notation of r=R', g=G' and b=B', and solving yields:

$C_0=1/(7*g^2*b^2*r^2+g^2*b^4-2*g^2*b^3*r-2*g*r^3*b^2+r^4*b^2+g^4*r^2-2*g^3*r^2*b+g^4*b^2-2*g^3*b^2*r-2*g*b^3*r^2+b^4*r^2-2*g^2*b*r^3+g^2*r^4)^(1/2)*r*b*g$ $C_0=-1/(7*g^2*b^2*r^2+g^2*b^4-2*g^2*b^3*r-2*g*r^3*b^2+r^4*b^2+g^4*r^2-2*g^3*r^2*b+g^4*b^2-2*g^3*b^2*r-2*g*b^3*r^2+b^4*r^2-2*g^2*b*r^3+g^2*r^4)^(1/2)*r*b*g$ $C_1=1/(7*g^2*b^2*r^2+g^2*b^4-2*g^2*b^3*r-2*g*r^3*b^2+r^4*b^2+g^4*r^2-2*g^3*r^2*b+g^4*b^2-2*g^3*b^2*r-2*g*b^3*r^2+b^4*r^2-2*g^2*b*r^3+g^2*r^4)^(1/2)*b*g*(b-r)$ $C_1=-1/(7*g^2*b^2*r^2+g^2*b^4-2*g^2*b^3*r-2*g*r^3*b^2+r^4*b^2+g^4*r^2-2*g^3*r^2*b+g^4*b^2-2*g^3*b^2*r-2*g*b^3*r^2+b^4*r^2-2*g^2*b*r^3+g^2*r^4)^(1/2)*b*g*(b-r)$ $C_2=-1/(7*g^2*b^2*r^2+g^2*b^4-2*g^2*b^3*r-2*g*r^3*b^2+r^4*b^2+g^4*r^2-2*g^3*r^2*b+g^4*b^2-2*g^3*b^2*r-2*g*b^3*r^2+b^4*r^2-2*g^2*b*r^3+g^2*r^4)^(1/2)*r*b*(g-r)$ $C_2=1/(7*g^2*b^2*r^2+g^2*b^4-2*g^2*b^3*r-2*g*r^3*b^2+r^4*b^2+g^4*r^2-2*g^3*r^2*b+g^4*b^2-2*g^3*b^2*r-2*g*b^3*r^2+b^4*r^2-2*g^2*b*r^3+g^2*r^4)^(1/2)*r*b*(g-r)$ $C_3=1/(7*g^2*b^2*r^2+g^2*b^4-2*g^2*b^3*r-2*g*r^3*b^2+r^4*b^2+g^4*r^2-2*g^3*r^2*b+g^4*b^2-2*g^3*b^2*r-2*g*b^3*r^2+b^4*r^2-2*g^2*b*r^3+g^2*r^4)^(1/2)*r*g*(g-b)$ $C_3=-1/(7*g^2*b^2*r^2+g^2*b^4-2*g^2*b^3*r-2*g*r^3*b^2+r^4*b^2+g^4*r^2-2*g^3*r^2*b+g^4*b^2-2*g^3*b^2*r-2*g*b^3*r^2+b^4*r^2-2*g^2*b*r^3+g^2*r^4)^(1/2)*r*g*(g-b)$ $C_4=1/(7*g^2*b^2*r^2+g^2*b^4-2*g^2*b^3*r-2*g*r^3*b^2+r^4*b^2+g^4*r^2-2*g^3*r^2*b+g^4*b^2-2*g^3*b^2*r-2*g*b^3*r^2+b^4*r^2-2*g^2*b*r^3+g^2*r^4)^(1/2)*b*g*(g-r)$ $$C_4 = -1/(7*g^2*b^2*r^2 + g^2*b^4 - 2*g^2*b^3*r - 2*g*r^3*b^2 + r^4*b^2 + g^4*r^2 - 2*g^3*r^2*b + g^4*b^2 - 2*g^3*b^2*r - 2*g*b^3*r^2 + b^4*r^2 - 2*g^2*b*r^3 + g^2*r^4)^{(1/2)} * b*g*(g-r)$$

$$C_5 = -1/(7*g^2*b^2*r^2 + g^2*b^4 - 2*g^2*b^3*r - 2*g*r^3*b^2 + r^4*b^2 + g^4*r^2 - 2*g^3*r^2*b + g^4*b^2 - 2*g^3*b^2*r - 2*g*b^3*r^2 + b^4*r^2 - 2*g^2*b*r^3 + g^2*r^4)^{(1/2)} * r*b*(g-b)$$

$$C_5 = 1/(7*g^2*b^2*r^2 + g^2*b^4 - 2*g^2*b^3*r - 2*g*r^3*b^2 + r^4*b^2 + g^4*r^2 - 2*g^3*r^2*b + g^4*b^2 - 2*g^3*b^2*r - 2*g*b^3*r^2 + b^4*r^2 - 2*g^2*b*r^3 + g^2*r^4)^{(1/2)} * r*b*(g-b)$$

$$C_6 = -1/(7*g^2*b^2*r^2 + g^2*b^4 - 2*g^2*b^3*r - 2*g*r^3*b^2 + r^4*b^2 + g^4*r^2 - 2*g^3*r^2*b + g^4*b^2 - 2*g^3*b^2*r - 2*g*b^3*r^2 + b^4*r^2 - 2*g^2*b*r^3 + g^2*r^4)^{(1/2)} * r*g*(b-r)$$

$$C_6 = 1/(7*g^2*b^2*r^2 + g^2*b^4 - 2*g^2*b^3*r - 2*g*r^3*b^2 + r^4*b^2 + g^4*r^2 - 2*g^3*r^2*b + g^4*b^2 - 2*g^3*b^2*r - 2*g*b^3*r^2 + b^4*r^2 - 2*g^2*b*r^3 + g^2*r^4)^{(1/2)} * r*g*(b-r) \quad (8).$$

Example 7

Extracting Biophysical and/or Biochemical and/or Substance Measurement Data from the Biophysical Metaparameters In the present example, the desired biochemical, biophysical, and/or physiological properties $S_u(t)$ are computed from the biophysical meta-parameters, where the subscript u denotes the name of the property computed (e.g. glucose level, O2 level, etc). Towards this end, for each local biophysical or physiological parameter $s_u$, at a pixel (I,J), an iterative computation process is defined as follows:

$$S_u^{I,J}(t) = Q[R_m^u(\{\overline{C^{I',J'}(t')}\}), R', G', B')] \quad (9)$$

where M is a chosen constant, the iteration number m is given by m=1, 2, , , M, $s_u^{I,J}(t)$ denotes the biophysical or physiological computed locally for pixel (I,J), $\{\overline{C^{I',J'}(t)}\}$ denotes the set of biophysical meta-parameter vectors at pixel (I',J'). In some embodiments, pixel (I',J') is in the vicinity of pixel (I,J). The operator $R_m^u$ defines the spatial, temporal or spatial-temporal iteration process and the Q operator is chosen according to the specific $R_m^u$ under consideration. It is noted that the operators $R_m^u$ and Q are chosen specifically each for biophysical, biochemical or physiological parameter under consideration (heartbeat, blood pressure, oxyhemoglobin, pH, carbon dioxide, moister, clarity, glucose, color vividness and/or saturation, etc.) For example, Q is chosen to be a normalized integral over all spatial or temporal or spatial-temporal results of the iteration process. The time vector $\bar{t}$ represents the set of temporal solutions $t_1, t_2, , ,$ to the current state t.

An exemplary $R_m^u$ for the specific case wherein the subscript u denotes the heartbeat vital life sign (such as a pulse) is a noise reduction process following by a derivative and a temporary correlation process on the spatial averaging of the vector C in order to find the irregularity in the temporal sequence C for the detecting the heartbeat signal.

The general process defined in (9) involves for each biophysical or physiological estimated parameter a process involving spatial, temporal or spatial-temporal analysis incorporating the mathematical operations such as algebraic, derivative, iterative, correlation, cross correlation, autocorrelation, averaging, multiplication, addition, functional composition, linear or non linear combination, noise reduction, etc. for obtaining the set of biophysical, biochemical or physiological parameters.

Other life sign to be computed such as skin tissue capillaries oxygen or carbon dioxide concentration or skin capillary systolic or diastolic blood pressure, skin pH, moister, dryness, etc. with for example various sets of solutions $\overline{C_{ij}^n}(t)$ (n=1, 2, , , L) where L is defined according to the number of biophysics or physiological parameters to be estimated from the signal. The process $R_m^u$ is designed according to the desire parameter under consideration. The choice of u is indicating the type of process to be applied as for example the skin capillaries oxygen concentration, or the carbon dioxide concentration, etc.

Example 8

Extracting Biophysical and/or Biochemical Measurement Data from the Biophysical Metaparameters—A Specific Case The present inventor has found that a particular form of equation (9) can be used to extract estimated biophysical and/or biochemical and/or physiological measurements from the biophysical meta-parameters. This particular expression is given by $$s_u^{I,J}(t) = Q\left\{ H_1 + H_6 \frac{H_2 + H_3 \sum_{j=1}^{N} \sum_{i=0}^{L} W_i^u(j) C_{ij}^{I',J'}(t')}{H_4 + H_5 \sum_{j=1}^{N} \sum_{i=0}^{L} V_i^u(j) C_{ij}^{I',J'}(t')} \right\} \quad (10A)$$

Q in this case is an average over all spatial-temporal pixels (I',J',t') under consideration. $H_1$, $H_2$, $H_3$, $H_4$, $H_5$, and $H_6$ are real free constants determined according the particular u or parameter to be determined $W^u$ and $V^u$ are two different sets of parameters defining the linear combination for specific u or parameter to be determined such as skin capillaries oxygen concentration and skin capillaries carbon dioxide concentration, or skin capillary systolic or diastolic blood pressure, etc. It is important to note that the estimated parameter only reflects a local measurement at pixels (I,J) at time t. In other words, in case we measure the skin capillary systolic or diastolic blood pressure parameters over 2×2 square millimeters of facial skin area, the estimated result shall reflects the measurements only in that particular area. In this example, pixels I',J' are within the 2×2 square millimeters of facial skin area.

Example 8

Look Up Tables

The present inventor is now disclosing that one useful particular form of (9) is of using $R_m^u$ to be histogram look up table over the computed $\{\overline{C^{I',J'}(t)}\}$ and Q averaging over certain period of time and all pixels under consideration. Let m=1 having one iteration and let $C_0, C_1, , , C_6$ of equation (8) be under consideration then from (9) we observe $$s_u(t) = Q(R_1^u(C_0^{I',J'}(t'), C_1^{I',J'}(t'), \ldots C_6^{I',J'}(t'))) \quad (10B).$$

Let u represents for example Glucose biomarker. Su provides the color absorption as emphasized by the Cs form a UV to up IR light spectrum transverse a soft tissue. The shape and width of the Su look up table(s) provide the information related to blood glucose variation.

There are various ways to generate different histograms where each histogram may be indicative of a given absorption and/or light distribution throughout the tissue, and may be useful for monitoring concentrations and/or biophysical parameters. It is noted that it may be useful to compute temporal variations in the histogram/lookup table (for example, for measuring stroke volume and/or blood pressure).

The above example, is useful for determining temporarily blood sugar level.

Example 10

Coefficients for the Specific Case of Measuring Skin Oxygen Saturation

For the following particular example of an un-normalized skin capillary oxygen saturation which is indirectly related to the red color and using the Sony camera model PCB-EX780 with optical zoom and day room light, the following particular form of eqns. 9, 10 was used:

$$S_{skin\_oxygen\_saturation}^{I,J}(t) = C_{2,1}^{I,J}(t) + C_{5,1}^{I,J}(t) + C_{6,1}^{I,J}(t) - C_{3,1}^{I,J}(t) \quad (11)$$

The above particular solution is not unique and additional variations are also possible.

Example 11

Choosing the Coefficients $H_1$-$H_6$ and the Vectors $V_\alpha^n$, $W_\alpha^n$ In this example, a general prescription for choosing coefficients $H_1$-$H_6$ and the vectors $V_\alpha^n$, $W_\alpha^n$ is presented.

Having a-priory information such as invasive blood test or from non invasive devices such as oximeter, blood pressure, pH sticks, etc. as reference to the current system it is simple to find by solving algebraic or functional equations which vector combination satisfies the relative a-priori measurements.

$$A\_Priori\_Result(t) = Q\left[H_1 + H_6 \frac{H_2 + H_3 \sum_n \sum_{\alpha=0}^L W_\alpha^u(n) C_\alpha^n(t)}{H_4 + H_5 \sum_n \sum_{\alpha=0}^L V_\alpha^u(n) C_\alpha^n(t)}\right]. \quad (12)$$

It important to understand the role of the vector C, which provides certain relationship between the subject colors such the skin and the unknown physiological/biophysical parameter. For example in case CO2 is increased in which indirectly influence the blue color it is suggest to look over the coefficients C1, C2 and C5 as an indicator for CO2 level.

Once again, eq. (9) reflect general process to compute from the vector C the unknown physiological/biophysical parameters. Eq. (9) may represent process involving interpolation, derivative, algebraic operation, etc.

Example 12

Measuring a Pulse Rate Using Oximeters

In order to compute heartbeat, there must be sufficient temporal sampling. According to Nyquist sampling theory, assuming heartbeat rate up to say 240 BPM (Beat Per Minute), at least 8 frames per second are necessary in order to derive a heartbeat rate from a information vector C. In some embodiments, it is recommended to use a greater sampling rate.

The heartbeat pulse is estimated directly from the R'G'B' color space or indirectly from the solution vector C. The following is an example for the computation of heartbeat pulse from the solution vector C (can be applied directly over the R'G'B' space)

a. Sample local skin area according to Nyquist rate for duration says 5 seconds.
b. Compute the solution (7) for each pixel in local skin frame.
c. Take spatial average of all pixel solution in local skin frame
d. Reduce noise
e. Search for temporary pulse pattern, one may use FFT to recognize cyclic patterns.
f. Use for example Derivative, FIR or IIR, max and min operations.
g. Screen the behavior of the pulse and the aggregate number of pulses during one minute.

Repute the process for new temporary duration

Example 13

A Discussion of Various Measured Parameters

Just as in Oximeter, the oxygen level is provided in percentage, i.e. how much the hemoglobin is saturated or desaturated by oxygen. Equivalently our case for CO2 or O2 how much the skin capillary cells are saturated or desaturated by CO2 or O2. Now if we say O2 is 100% we mean that the skin capillary cells are 100% saturated by oxygen. In case we say CO2 is 100% implies that the skin capillary cells are 100% saturated by carbon dioxide which is impossible, unless the person is really dead. We have found out that normal range is between 2% to 20% for CO2. Below 2% and over 20% are abnormal situations. In case of oxygen normal range is 80% to 100%. Out of this range implies on irregularity of the local skin area.

Dryness: x % (0 . . . 100 or 0 . . . 1) means dryness level of the measured local area (e.g. skin area). For example x=40% the measured local area is over dehydrated. Normal range is 15 . . . 25%. The range between 25% to 30% is little bit dry and over 30% is dehydrated. It should be noted that the water absorption in skin is not directly absorbed due to pH and oiliness and it requires certain molecules to transmit the water into the skin. This varies from person to person.

Moisture Oily/regular/dry: x % (0 . . . 100 or 0 . . . 1) means the oiliness level of the measured local area. It is customize to say oily, regular or dry in the sense of skin oiliness. The skin oiliness is produced by special under skin oil glands. In case x=5% the local area (e.g. skin local area) moisture is very dry. Typical normal range is 10% to 30% oiliness level where below 10% is too dry and over 30% is too oily.

The local area is always close area such as square, circle or elliptic area. In such cases the dimension could be in cm2 or mm2 or pr2. If we measure from two different sources (like two cameras) we are able to provide cubic local area.

Below is an exemplary list of properties that can be measured according to embodiments of the present invention.
Properties Related to a Mammalian Subject
   a. Oxygen and Carbon Dioxide concentration,
   b. Urea nitrogen,
   c. Systolic and Diastolic blood pressure,
   d. Moisture, e. Dryness,
f. Saltiness,
g. Glucose
h. pH
i. Tissue saturation (for example external Skin tissue, internal muscle)
j. Tissue vitality (for example internal tumor tissue or external skin melanoma represents different skin vitality)
k. Red Cells Count (number or concentration of cells per one cubic millimeter)
l. Stroke Volume Variation (amount of blood injecting out from the heart in every stroke) and
m. Skin vessel deformation Skin disease such as psoriasis or melanoma, body disease such as hepatitis, kidney, heart failure are all influence the skin cell colors. With the following example of melanoma we see different measurements indicating on skin disease. Using this invention in every house shall provide first diagnostic about the body condition.

Therefore, the degree of arterial sclerosis, or the blood pressure, of the subject can be estimated with high accuracy based on the thus determined pulse-wave propagation velocity.

Properties Related to Food, Beverage and/or Plant Matter

From a local skin surface or other local tissue less area such as wine in sealed bottle can be estimated from eq. (12) by choosing specific coefficients vectors $W^\alpha$ and $V^\alpha$. The way we compute those specific vectors is by getting a priori information about the object under consideration. For example, wine oxygen concentration requires different Example 14

Experimental Data

14a. Skin Tissue Blood Pressure
Number of Patients: 33
Ages: 13 to 58
Reference: Blood Pressure comparison Indicator: auto blood pressure A&D Japan model UA767
Light Condition: Room day light
Video Camera: Sony NTSC Video Camera model PCB-EX780
Error: The distance between the reference device and our digital system
Interval Distance Error: 5
14b. Face Skin Tissue HeartBeat
Number of Patients: 33
Ages: 13 to 58
Reference: Comparison with Compumedics SOMTE' Heartbeat Pulse Oximeter and blood pressure A&D Japan model UA767
Light Condition: Room day light
Video Camera: Sony NTSC Video Camera model PCB-EX780
Error: distance between the reference device and our measurement digital system
Interval Distance Error: 5
14c. Skin Tissue Oxygen
Number of Patients: 33
Ages: 13 to 58
Reference: Comparison with Compumedics SOMTE' Heartbeat Pulse Oximeter
Light Condition: Room day light
Video Camera: Sony NTSC Video Camera model PCB-EX780
Error: distance between the reference device and our digital system
Interval Distance Error: Dynamic, 0.4, 0.6, 1, 1.2
14d. Skin Tissue PH
Number of Patients: 33
Ages: 13 to 58
Reference: pH sticks indicator (4.5 to 10) made by Riedel-DeHaen Germany
Light Condition: Room day light
Video Camera: Sony NTSC Video Camera model PCB-EX780
Error: distance between the reference device and our measurement digital system
Interval Distance Error: Dynamic, 0.4, 0.6, 1

Example 15

Determination of Biophysical and Biochemical Parameters from Historical Data

For example: A 40 years age person who was video taped at his 10 years age and the video tape was stored in good conditions provides physiological information about the time that the 40 years age person was at age 10. Such ability is highly important for tracking historical unavailable physiological record from video tape in genetic disease such as cancer, heart failure, etc.

Thus, it is noted that the subject need not even be alive, and the image processing unit and/or optional instruction data are configured to provide historical physiological information about the subject at the time of imaging.

Example 16

Independent Experimental Validation

A heartbeat and Glucose test performed independently over 28 volunteers. The test conducted in two separated rooms where each volunteer was first tested with the current invention by using simple video camera free of any contact and following the volunteer move to the second room and was tested by EMT. The gap in the measurements is generated since the test was not conducted simultaneously. Yet the results are promising and showing that the invention is working.

Example 17

Skin absorption potential is a parameter depending for example on at least local moisture level and pH level (the pH level reflects certain connection to the dielectric characteristic of the local skin area) which represents certain resistance). Other parameters may include for example Co2 and O2 levels. A weighted combination of these parameters represents a local potential of the skin to absorb various skin treatment.

Example 18

Experimental Test for Melanoma

A Three rectangular skin tissue spots (FIGS. 18a, 18b and 18c) relatively close to each other has been tested. One of the spots (FIG. 18c) is having oxygen and pH biophysical measurement relatively high than the others. Following medical diagnostic that particular spot was detected as melanoma.

Example 18

A Brief Discussion of Photodetectors

The following describe the distribution functions of light sensed by the human retina photoreceptors called cones and probes. We focus on the cones.

Let $a_i(C)$ represent the spectral color response observed by the retina three cones receptors type having spectra absorption distribution $S_i(\lambda)$ i=1, 2, 3 respectively with certain overlapping between the absorption distribution functions, particularly between $S_1$ and $S_2$ i.e. Red and Green. The visible color sensation is define in the range $$\lambda_{min} \leq \lambda \leq \lambda_{max} \text{ and } \lambda_{min} \cong 380 \text{ nm and } \lambda_{max} \cong 780 \text{ nm}, \quad (A1)$$

and is described by the spectral responses $$a_i(C) = \int_0^\infty S_i(\lambda) C(\lambda) d\lambda \quad (A2)$$

The retina cones visual spectra distributions of $S_1$, $S_2$ and $S_3$ are decaying outside the spectral bandwidth $[\lambda_{min}, \lambda_{max}]$. From eq. (A2) we can learn that two spectral distribution $C(\lambda_1)$ and $C(\lambda_2)$ may produces identical spectral response $a_i(C_1)=a_i(C_2)$ for i=1, 2, 3. This means that two colors that look identical could have different spectral distribution.

Using primary colors we observe from (A2) that the color matching coefficients $h_{ij}$ are computed as follows $$h_{ij} = a_i(P_k) = \int_0^\infty S_i(\lambda) P_k(\lambda) d\lambda \quad (A3)$$
$$k = 1, 2, 3$$

Where each primary color distribution (i.e. k=1,2,3) represent one of the basic colors (i.e. R, G or B) or any other suitable set of basic colors. In addition we assume that each of the basic colors has unity energy distribution i.e. the integral over the domain λmin to λmax is unity. It follows that a color matching procedure involves solving the following equations:

$$\sum_{k=1}^{3} \varepsilon_k h_{ik} = a_i(C) = \int_0^\infty S_i(\lambda) C(\lambda) d\lambda \quad (A4)$$

This means given for example three primary colors $P_1$, $P_2$ and $P_3$ and the three type retina (cones) distribution functions $S_i(\lambda)$ the coefficient matrix is computed from the cross correlation distribution response given in (A2) and (A3). Given three numbers $\in_k$ the linear combination set in (A4) describes the color perceived as $C(\lambda)$.

Having the idea of color matching in the biophtodetector array (retina cones) we proceed with the physical photodetector array such as CCD. Without losing generality we assume that a photodetector array has $D_i(x,y,\lambda)$ color distribution function (i=1, 2, 3) for the three photodetector array marked as R,G,B (could be as well Yellow, Magenta or Cyan or any other finite set of colors or equivalent distribution functions). Let $I(\lambda,x,y)$ be the color intensity distributed object. The coordinate system (x,y) represent the photodetector coordinate system or the film coordinate system where every space point (X,Y,Z) representing the 3D real time manifold or real time scenario or environment is projected onto the film coordinate system having the following projection coordinate connections $$x = \xi \frac{X}{Z} \quad (A5)$$
$$y = \xi \frac{Y}{Z}$$

where $\xi$ represents the focal length of the film plane.

The photodetector array distribution response function is given mutatis mutandis to (A2) as follows:

$$\sum_{k=1}^{3} v_k(x, y) q_{ik}(x, y) = g_i(x, y, I) = \int_0^\infty D_i(x, y, \lambda) I(x, y, \lambda) d\lambda \quad (A6)$$

Where $g_i(x,y,I)$ represent the (x,y) photodetector cell response to the object I. Marking by $R=g_1(x,y,I)$, $G=g_2(x,y,I)$ and $B=g_3(x,y,I)$ the cell response to the object I with respect to the color distribution $D_1$ for R, $D_2$ for G and $D_3$ for B of the photodetector array. The distribution functions are decaying outside a finite range, usually about 300 nm to 800 nm and in case of IR over 1200 nm and in case of thermo around 4000 nm.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

All references cited herein are incorporated by reference in their entirety. Citation of a reference does not constitute an admission that the reference is prior art.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

What is claimed is:

1. An image processing system for obtaining biophysical information about a mammalian subject, said image processing system comprising:
    an image receiving unit, including at least one image sensor, configured to receive a video electronic color image of a first tissue of the mammalian subject, the electronic color image comprising spatial temporal per pixel information for a visible red color space, spatial temporal per pixel information for a visible green color space and spatial temporal per pixel information for a visible blue color space, the electronic color image derived from light reflected from and/or traversing the first tissue, the light incident from a light source and having a wavelength between near UV and near IR; and an image processing unit configured for (a) electronically processing said image by transforming per pixel information for the red, green and blue visible colors to transformed per pixel information for the red, green and blue visible colors, (b) using the transformed per pixel information of at least one of the red, green and blue visible colors to produce (i) a histogram of intensity for each color of the at least one of the red, green and blue visible colors or (ii) both a histogram of intensity for each color of the at least one of the red, green and blue visible colors and an averaging of spatial per pixel information for each color of the at least one of the red, green and blue visible colors, and (c) extracting measurement data from the (i) histogram or (ii) both the histogram and the averaging, to obtain the biophysical information using an iterative process, the image processing system adapted to obtain the biophysical information whether the incident light incident on the first tissue from the light source is filtered or unfiltered, continuous or discontinuous, of a natural light source or of an artificial light source.

2. The image processing system of claim 1, wherein the image processing unit is configured to electronically process the image by extracting a level of a chemical concentration or saturation from the (i) histogram or (ii) both the histogram and the averaging.

3. The image processing system of claim 1, wherein said first tissue is selected from the group consisting of soft tissue, hard tissue, skin tissue, surface tissue, outer tissue, internal tissue, a membrane, fetal tissue, liquid tissue, and endothelial tissue.

4. The image processing system of claim 1, wherein said first tissue comprises at least one of skin tissue, liquid tissue, hard tissue and blood vessel tissue.

5. The image processing system of claim 1, wherein said biophysical information is a biophysical parameter selected from the group consisting of a heartbeat, a pulse transition time (PTT), stroke volume (SV), vessel deformation and a blood pressure.

6. The image processing system of claim 1, wherein said biophysical information is a biophysical parameter indicative of a physiological condition selected from the group consisting a physiological condition of the skin, a cardiovascular condition including stroke volume, vessel deformation information, heartbeat and oxygen saturation, a pulmonary condition, a physiological condition of an internal organ, a physiological condition of an organ associated with the digestive system, a physiological condition of the kidneys, a physiological condition of the liver, and a physiological condition of the blood including blood pressure.

7. The image processing system of claim 1, wherein said biophysical information is a biophysical parameter selected from the group consisting of oil moisture content of skin, skin dryness, skin clarity, tissue pH, hemoglobin, oxygen, carbon dioxide, bilirubin, blood viscosity, skin saturation, oxygen ($O_2$) saturation, carbon dioxide ($CO_2$) saturation, iron, urea nitrogen, white cells, platelets, glucose, skin glucose, skin absorption potential, skin pigmentation, red cells concentration, blood pressure, skin pH, skin saltiness level, collagen concentration, a condition related to skin smoothness, a condition related to skin saturation, a condition related to skin vitality, a condition related to sweat, and a condition related to skin wrinkles, a condition related to skin acne, a condition related to skin melanoma.

8. The system of claim 1, wherein the biophysical information is a condition of the liver, a condition of the kidney, cancer, skin cancer, a blood cancer, a nutritional deficiency, a loss of blood, a malignant condition, of bone marrow, dehydration, hepatitis, a physiological condition of a muscle, a presence of a microbe, a presence of an infectious microbe, an autoimmune condition, a presence of a fungus, and a pulmonary condition.

9. The system of claim 1, wherein the biophysical information concerns a substance and wherein the substance is at least one of a dissolved or partially dissolved substance within a bodily fluid within the mammalian subject an ion a substance indicative of pH a pigment, a waste product, a polymer, a complexed polymer, a biopolymer, a protein, a complexed protein, a complexed protein selected from the group consisting of a hemoglobin-oxygen complex and a hemoglobin-carbon dioxide complex, a saccharide, glucose.

10. The system of claim 1, wherein the image receiving unit includes at least one of: a CMOS image sensor and a CCD image sensor, a thermal sensor, an IR sensor, a visible light sensor, and a UV sensor, an array of photodetectors configured to sense light of a wavelength between 280 nm to 4500 nm.

11. The system of claim 1, wherein at least one of the first visible color, the second visible color and the third visible color represents a particular pixel value in the finite range wherein A and B are real numbers.

12. The system of claim 1, wherein the system is configured to store the video electronic color image of the first tissue for processing by the image processing unit at a later time.

13. An image processing system for obtaining chemical concentration or saturation of at least one of a tissue of a mammalian subject, a food item, a liquid or an environmental item, said image processing system comprising:

an image receiving unit, including at least one image sensor, configured to receive a video electronic color image of a first tissue of the mammalian subject, the electronic color image comprising spatial temporal per pixel information for a visible red color space, spatial temporal per pixel information for a visible green color space and spatial temporal per pixel information for a visible blue color space, the electronic color image derived from light reflected from and/or traversing the at least one of the tissue, food item, liquid or environmental item, the light incident from a light source and having a wavelength between near UV and near IR; and an image processing unit configured for (a) electronically processing said image by transforming per pixel information for the red, green and blue visible colors to transformed per pixel information for the red, green and blue visible colors, (b) using the transformed per pixel information of at least one of the red, green and blue visible colors to produce (i) a histogram of intensity for each color of the at least one of the red, green and blue visible colors or (ii) both a histogram of intensity for each color of the at least one of the red, green and blue visible colors and an averaging of spatial per pixel information for each color of the at least one of the red, green and blue visible colors, and (c) extracting measurement data from the (i) histogram or (ii) both the histogram and the averaging, to obtain the biophysical information using an iterative process, the image processing system device adapted to obtain the information about the chemical concentration or saturation whether the incident light incident on the first tissue from the light source is filtered or unfiltered, continuous or discontinuous, of a natural light source or of an artificial light source.

14. The image processing system of claim 13, wherein the tissue is selected from the group consisting of soft tissue, hard tissue, skin tissue, surface tissue, outer tissue, internal tissue, a membrane, fetal tissue, liquid tissue, and endothelial tissue and blood vessel tissue, and wherein said food or environmental item is at least one of a liquid, a hard item and a soft item.

15. The image processing system of claim 13, wherein said chemical concentration or saturation, whether dissolved or not dissolved, is of a parameter selected from the group consisting of an oxygen, oxygen saturation, red cells concentration, hemoglobin, hematocrit, pigment, carbon dioxide, CO2 saturation, bilirubin, a skin saturation, an iron, a polymer, a biopolymer, complex biopolymer, complex polymer, protein, complex protein, a concentration of an oily substance, nitrogen, urea nitrogen, skin saturation, a concentration or saturation of salt.

16. The image processing system of claim 13, wherein said chemical concentration or saturation is indicative of a physiological condition or status of the mammalian subject selected from the group consisting of a condition of the liver, a condition of the kidney cancer, a skin cancer, a blood cancer, a nutritional deficiency, a loss of blood, a malignant condition of bone marrow, dehydration, a cardiovascular condition, hepatitis, a physiological condition of a muscle, a heart rate, a blood pressure (systolic or diastolic), stroke volume, a presence of a microbe, a presence of an infectious microbe, an autoimmune condition, a presence of a fungus, and a pulmonary condition.

17. A non-transitory computer-readable storage medium containing computer-readable instruction data executable by a processing unit for obtaining at least one of (i) biophysical information, and (ii) a chemical concentration of at least one substance, in or on a mammalian subject, the instruction data comprising the instructions of:
   a. processing a video electronic color image of a first tissue of the mammalian subject by sensing a continuous spectrum of light having a wavelength between near UV and near IR, the electronic color image comprising spatial temporal per pixel information for a visible red color space, spatial temporal per pixel information for a visible green color space and spatial temporal per pixel information for a visible blue color space, the still or video color image derived from light reflected from and/or traversing the first tissue, the light incident from a light source having a wavelength between near UV and near IR; and
   electronically processing said video color image by transforming per pixel information for the red, green and blue visible colors to transformed per pixel information for the red, green and blue visible colors,
   using the transformed per pixel information of at least one of the red, green and blue visible colors to produce (i) a histogram of intensity for each color of the at least one of the red, green and blue visible colors or (ii) both a histogram of intensity for each color of the at least one of the red, green and blue visible colors and an averaging of spatial per pixel information for each color of the at least one of the red, green and blue visible colors, and
   extracting measurement data from the (i) histogram or (ii) both the histogram and the averaging, to obtain the biophysical information using an iterative process,
   b. the non-transitory computer-readable storage medium containing computer-readable instruction data for obtaining the biophysical information and/or the chemical concentration of the at least one substance, in or on the mammalian subject whether the light incident on the first tissue is from a continuous or discontinuous, filtered or unfiltered, natural or artificial, light source as a result of recognizing both filtered and unfiltered, continuous and discontinuous, and natural light sources and artificial light sources.

18. The non-transitory computer-readable storage medium of claim 17, wherein at least one of the first visible color, the second visible color and the third visible color represents a particular pixel value in the finite range wherein A and B are real numbers.

19. The non-transitory computer-readable storage medium of claim 17, wherein the system is configured to store the video electronic color image of the first tissue for processing by the image processing unit at a later time.

20. An image processing system for obtaining biophysical information about a mammalian subject, said image processing system comprising:
   an image receiving unit, including at least one image sensor, configured to receive a sequence of video electronic color images of a first tissue of the mammalian subject, each of the electronic color images comprising spatial temporal per pixel information for a visible red color space, spatial temporal per pixel information for a visible green color space and spatial temporal per pixel information for a visible blue color space, the electronic color images derived from light reflected from and/or traversing the first tissue, the light incident from a light source and having a wavelength between near UV and near IR; and
   an image processing unit configured for
   (a) electronically processing said images by transforming per pixel information for the red, green and blue visible colors to transformed per pixel information for the red, green and blue visible colors,
   (b) using the transformed per pixel information of at least one of the red, green and blue visible colors to produce an averaging of spatial per pixel information for each color of the at least one of the red, green and blue visible colors, and
   (c) extracting measurement data from the averaging to obtain the biophysical information using an iterative process,
   the image processing system adapted to obtain the biophysical information whether the incident light incident on the first tissue from the light source is filtered or unfiltered, continuous or discontinuous, of a natural light source or of an artificial light source.

* * * * *